US006635416B2

(12) United States Patent
Palese et al.

(10) Patent No.: US 6,635,416 B2
(45) Date of Patent: Oct. 21, 2003

(54) SCREENING METHODS FOR IDENTIFYING VIRAL PROTEINS WITH INTERFERON ANTAGONIZING FUNCTIONS AND POTENTIAL ANTIVIRAL AGENTS

(75) Inventors: Peter M. Palese, Leonia, NJ (US); Adolfo Garcia-Sastre, New York, NY (US); Christopher Basler, New York, NY (US)

(73) Assignee: Mount Sinai School of Medicine of New York University, New York, NY (US)

( * ) Notice: Subject to any disclaimer, the term of this patent is extended or adjusted under 35 U.S.C. 154(b) by 0 days.

(21) Appl. No.: 09/829,711

(22) Filed: Apr. 10, 2001

(65) Prior Publication Data

US 2002/0090608 A1 Jul. 11, 2002

Related U.S. Application Data

(60) Provisional application No. 60/195,465, filed on Apr. 10, 2000.

(51) Int. Cl.[7] ............................. C12Q 1/70; C12Q 1/02; C12N 7/00
(52) U.S. Cl. .......................... 435/5; 435/29; 435/235.1; 435/236
(58) Field of Search ........................ 435/5, 29, 235.1, 435/236

(56) References Cited

FOREIGN PATENT DOCUMENTS

| DE | 100 20 505 | * 10/2001 | .......... A61K/38/00 |
|----|------------|-----------|----------------------|
| WO | WO 97/08292 | 3/1997 | |
| WO | WO 99/64068 | 12/1999 | |
| WO | WO 99/64570 | 12/1999 | |
| WO | WO 99/64571 | 12/1999 | |

OTHER PUBLICATIONS

Beattie et al (Journal of Virology 69:499–505, 1995).*

Bossert et al., 2002, "Respiratory Syncytial Virus (RSV) Nonstrucutral (NS) Proteins as Host Range Determinants: a Chimeric Bovii RSV with NS Genes from Human RSV Is Attenuated in Interferon–Competent Bovine Cells", J. of Virology 76:4287–93.

Schlender et al., 2000, "Bovine Respiratory Syncytial Virus Nonstructural Proteins NS1 and NS2 Coooperatively Antagonize Alpha/Beta Interferon–Induced Antiviral Response", J. of Virology 74:8234–8242.

(List continued on next page.)

Primary Examiner—Mary E. Mosher
(74) Attorney, Agent, or Firm—Pennie & Edmonds LLP

(57) ABSTRACT

The present invention relates, in general, to a screening method for identifying novel viral proteins with interferon antagonizing function using a transfection-based assay, and the use of such proteins in isolating various types of attenuated viruses for the development of vaccine and pharmaceutical formulations. The invention also relates to the use of viral interferon antagonists in screening assays to identify potential anti-viral agents. The invention further relates to protocols utilizing interferon antagonists, e.g., NS1, to enhance gene therapy or DNA vaccination based on their ability to increase gene expression.

17 Claims, 6 Drawing Sheets

OTHER PUBLICATIONS

Figure 3A:
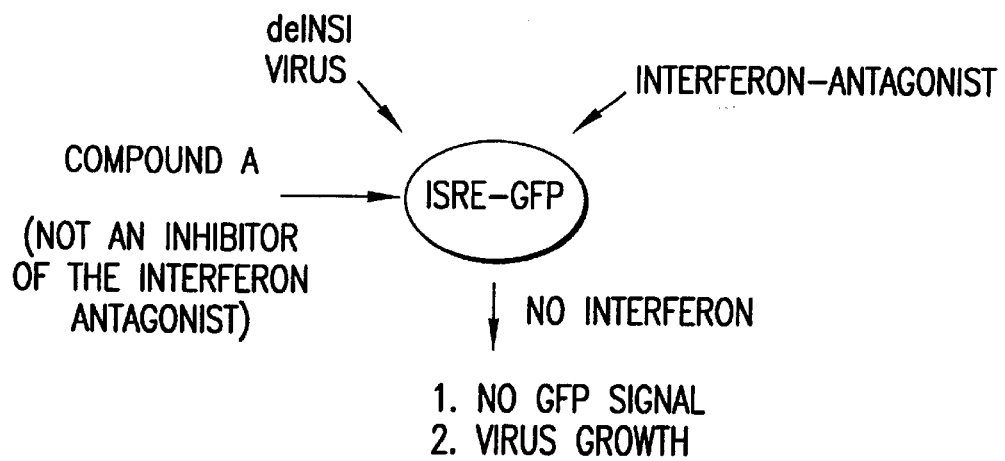

Butterfield and Campbell, 1978, "Vaccination for Fowl Plague", Selected Reports and Notes, 671–674.

Clemens and Elia, 1997, "The Double Stranded RNA–Dependent Protein Kinase PKR: Structure and Function", Journal of Interferon and Cytokine Research, 17:503–524.

Didcock et al., 1999, "The V Protein of Simian Virus 5 Inhibits Interferon Signalling by Targeting STAT1 for Proteasome–Mediated Degradation", J. of Virology, 73(12): 9928–9933.

Floyd–Smith et al., 1981, "Interferon Action: RNA Cleavage Pattern of a (2'–5') Oligoadenylate–Dependent Endonuclease", Science 212: 1030–1032.

Garcia–Sastre et al., 1998, "The Role of Interferon in Influenza Virus Tissue Tropism", J. of Virology, 72(11): 8550–8558.

Garcia–Sastre et al., 1998, "Influenza A Virus Lacking the NS1 Gene Replicates in Interferon–Deficient System", Virology 252:324–330.

Garcin et al., 1999, "Sendai Virus C Proteins Counteract the Interferon–Mediated Induction of an Antiviral State", J. Virology 73(8): 6559–6565.

Gotoh et al., 1999, "Knockout of the Sendai Virus C Gene Eliminates the Viral Ability to Prevent the Interferon–$\alpha$/$\beta$–Mediated Responses", FEBS Letters 459:205–210.

Haller et al., 1998, "Mx Proteins: Mediators of Innates Resistance to RNA Viruses", Rev. Sci. Tech. Off. Int. Epiz., 17(1):220–230.

Hatada and Fukuda, 1992, "Binding of influenza A virus NS1 protein to dsRNA in vitro", J. of General Virology, 73: 3325–3329.

He et al., 1997, "The 34.5 Protein Of Herpes Simplex Virus 1Complexes With Protein Phosphatase 1$\alpha$ to Dephosphorylate the $\alpha$ subunit of the eukaryotic translation factor 2 and preclude the shutoff of protein synthesis by double stranded RNA–activated protein kinase", Proc. Natl. Acad. Sci. USA, 94:843–848.

Komatsu et al., 2000, "Sendai Virus Blocks Alpha Interferon Signaling To Signal Transducers and Activators of Transcription", J. Virology, 74(5):2477–2480.

Lu et al., 1995, "Binding of the Influenza Virus NS1 Protein to Double Stranded RNA Inhibits the Activation of the Protein Kinase that Phosyphorylates the elF–2 Translational Factor", Virology 214:22–228.

Naniche et al., 2000, "Evasion of Host Defenses by Measles Virus: Wild Type Measles Virus Infection Interferes with Induction of Alpha/Beta Interferon Production", J. Virology, 74(16):7478–7484.

Norton et al., 1987, "Infectious Influenza A and B Virus Variants with Long Carboxyl Terminal Deletions in the NS1 Polypeptides", Virology 156:204–213.

Schnelder et al., 2000 "Bovine Respiratory Synctial Virus Nonstructural NS1 and NS2, Cooperatively Antagonize Alpha/Beta Interferon–Induced Antiviral Response", J. of Virology, 74(18):8234–8242.

Stark et al., 1998, "How Cells Respond to Interferons", Annu.Rev.Biochem. 67:227–264.

Talon et al., 2000, "Activation of Inteferon Regulatory Factor 3 Is Inhibited by the Influenza A Virus NS1 Protein", J. Of Virology, 74(17):7989–7996.

Talon et al., 2000 "Influenza A and B Viruses Expressing Altered NS1 Proteins: A vaccine Approach", Proc. Natl. Acad. Sci. USA 97(8):4309–4314.

Wang et al., 2000, "Influenza A Virus NS1 Protein Prevents Activation of NF–KB and Induction of Alpha/Beta Interferon", J. of Virology, 74(24): 11566–11573.

Yoshida et al., 1981, "Characterization of the RNA Associated with Influenza A Cytoplasmic Inclusions and the Interaction of $NS_1$ Protein with RNA", Virology 110: 87–97.

Young et al., 2000 "Paramyxoviridae Use Distinct Virus Specific Mechanisms to Circumvent the Interferon Response", Virology, 269:383–390.

* cited by examiner

```
              EMPTY VECTOR              INTERFERON-ANTAGONIST
                    │                    EXPRESSION PLASMID
                    │                           │
                    ▼        delNSI VIRUS       ▼        delNSI VIRUS
                  ╱───╲      ╱                ╱───╲      ╱
         CELL   (  ·  )  ←                CELL (  ·  )  ←
                  ╲───╱                        ╲───╱
                    │                           │
                    ▼                           ▼
           INTERFERON RESPONSES          NO INTERFERON RESPONSES
                    │                           │
                    ▼                           ▼
                NO VIRUS                      VIRUS
```

FIG.1

```
    PLASMID
   ENCODING                ╱───╲
  INTERFERON-   ─────→    (CELL)  ←───── INTERFERON-SENSITIVE VIRUS
   ANTAGONIST              ╲───╱
                             │
                             ▼
                         ENHANCED
                        VIRUS GROWTH
```

SCREENING METHODS FOR IDENTIFYING VIRAL PROTEINS WITH INTERFERON ANTAGONIZING FUNCTIONS AND POTENTIAL ANTIVIRAL AGENTS

This application is entitled to and claims priority benefit to U.S. provisional application Serial No. 60/195,465, filed on Apr. 10, 2000.

1. INTRODUCTION

The present invention relates, in general, to a screening method for identifying novel viral proteins with interferon antagonizing function, and the use of such proteins in isolating various types of attenuated viruses for the development of vaccine and pharmaceutical formulations. The invention also relates to the use of viral interferon antagonists in screening assays to identify potential anti-viral agents. The invention further relates to protocols utilizing interferon antagonists, e.g., NS1, to enhance gene therapy or DNA vaccination based on their ability to increase gene expression.

2. BACKGROUND OF THE INVENTION

One important component of the host antiviral response is the type I IFN system. Type I IFN is synthesized in response to viral infection. Double stranded RNA (dsRNA) or viral infection activate latent transcription factors, including IRF-3 and NF-$_k$B, resulting in transcriptional up-regulation of type I IFN, IFN-α, and IFN-β genes. Secreted type I IFNs signal through a common receptor, activating the JAK/STAT signaling pathway. This signaling stimulates transcription of IFN-sensitive genes, including a number of that encode antiviral proteins, and leads to the induction of an antiviral state. Among the antiviral proteins induced in response to type I IFN are dsRNA-dependent protein kinase R (PKR), 2',5'-oligoadenylate synthetase (OSA), and the Mx proteins (Clemens et al., 1997 Interferon Cytokine Res. 17:503–524; Floyd-Smith et al., 1981 Science 212:1030–1032; Haller et al., 1998 Rev. Sci Tech 17:220–230; Stark et al., Annu Rev. Biochem 67:227–264).

Many viruses have evolved mechanisms to subvert the host IFN response. For example, the herpes simplex virus counteracts the PKR-mediated phosphorylation of translation initiation factor cIF-2α, preventing the establishment of an IFN-induced block in protein synthesis (Garcia-Sastre et al. 1998 Virology 252 (2):324–30). In the negative-strand RNA viruses, several different anti-IFN mechanisms have been identified (Garcia-Sastre et al., 1998 Virology 252:324–330).

Citation of a reference in this section or any section of this application shall not be construed as an admission that such reference is prior art to the present invention.

3. SUMMARY OF THE INVENTION

The invention relates to screening methods for viral proteins with interferon antagonizing function based on transfection-based assays using various types of negative strand RNA viruses. The identified interferon antagonists can be used for several applications. The invention relates to attenuated viruses having an impaired ability to antagonize the cellular interferon (IFN) response, and the use of such attenuated viruses in vaccine and pharmaceutical formulations. Further, the present invention relates to viruses which have been mutated to impair the virus's ability to antagonize cellular interferon responses, impaired viruses or viruses with impaired interferon antagonist activity. The present invention also relates to growth substrates which support the growth of viruses, both naturally occurring and mutagenized, which have an impaired ability to antagonize the cellular interferon response, for diagnostic or therapeutic purposes.

The present invention relates to transfection-based assays to identify viral proteins with interferon-antagonizing activities. Once such viral proteins have been identified, genes encoding these proteins can be targeted to create attenuated viruses for the development of vaccines. Further, the viral proteins identified to have interferon-antagonizing activities can be used to support the growth of viruses with impaired abilities to antagonize cellular interferon responses for diagnostic, therapeutic or research protocols.

In a preferred embodiment, the present invention relates to screening assays to identify potential antiviral agents which inhibit the ability of the virus to antagonize cellular interferon responses. Thus, the identified viral proteins which antagonize interferon responses will also have utility in screening for and developing novel antiviral agents.

The present invention also relates to the substrates designed for the isolation, identification and growth of viruses for vaccine purposes as well as diagnostic and research purposes. In particular, interferon-deficient substrates for efficiently growing influenza virus mutants are described. In accordance with the present invention, an interferon-deficient substrate is one that is defective in its ability to produce or respond to interferon. The substrate of the present invention may be used for the growth of any number of viruses which may require interferon-deficient growth environment.

Furthermore, cell lines expressing viral proteins with interferon-antagonizing properties are encompassed by the present invention. These proteins include, for example, NS1 and other analogous proteins originating from various types of viruses. Such viruses may include, but are not limited to paramyxoviruses (Sendai virus, parainfluenza virus, mumps, Newcastle disease virus), morbilliviruses (measles virus, canine distemper virus and rinderpest virus); pneumoviruses (respiratory syncytial virus and bovine respiratory virus); rhabdoviruses (vesicular stomatitis virus and lyssavirus); RNA viruses, including hepatitis C virus and retroviruses, and DNA viruses, including vaccinia, adenoviruses, hepadna viruses, herpes viruses and poxviruses.

Any number of viruses may be used in accordance with the present invention, including DNA viruses, e.g., vaccinia, adenoviruses, hepadna viruses, herpes viruses, poxviruses, and parvoviruses; and RNA viruses, including hepatitis C3 virus, retrovirus, and segmented and non-segmented RNA viruses. The viruses can have segmented or non-segmented genomes and can be selected from naturally occurring strains, variants or mutants; mutagenized viruses (e.g., by exposure to UV irradiation, mutagens, and/or passaging); reassortants (for viruses with segmented genomes); and/or genetically engineered viruses. For example, the mutant viruses can be generated by natural variation, exposure to UV irradiation, exposure to chemical mutagens, by passaging in non-permissive hosts, by reassortment (i.e., by coinfection of an attenuated segmented virus with another strain having the desired antigens), and/or by genetic engineering (e.g., using "reverse genetics"). The viruses selected for use in the invention have defective IFN antagonist activity and are attenuated; i.e., they are infectious and can replicate in vivo, but only generate low titers resulting in subclinical levels of infection that are non-pathogenic. Such attenuated viruses are ideal candidates for live vaccines.

The invention is based, in part, on a number of discoveries and observations made by the Applicants when working with influenza virus mutants. However, the principles can be analogously applied and extrapolated to other segmented and non-segmented negative strand RNA viruses including, but not limited to paramyxoviruses (Sendai virus, parainfluenza virus, mumps, Newcastle disease virus), morbilliviruses (measles virus, canine distemper virus and rinderpest virus); pneumoviruses (respiratory syncytial virus and bovine respiratory virus); and rhabdoviruses (vesicular stomatitis virus and lyssavirus), and vaccinia, adenoviruses, hepadna viruses, herpes viruses and poxviruses.

First, the IFN response is important for containing viral infection in vivo. The Applicants found that growth of wild-type influenza virus A/WSN/33 in IFN-deficient mice (STAT1−/− mice) resulted in pan-organ infection; i.e., viral infection was not confined to the lungs as it is in wild-type mice which generate an IFN response (Garcia-Sastre, et al., 1998, J. Virol. 72:8550, which is incorporated by reference herein in its entirety). Second, the Applicants established that NS1 of influenza virus functions as an IFN antagonist.

The invention also relates to the use of the attenuated virus of the invention in vaccines and pharmaceutical preparations for humans or animals. In particular, the attenuated viruses can be used as vaccines against a broad range of viruses and/or antigens, including but not limited to antigens of strain variants, different viruses or other infectious pathogens (e.g., bacteria, parasites, fungi), or tumor specific antigens. In another embodiment, the attenuated viruses, which inhibit viral replication and tumor formation, can be used for the prophylaxis or treatment of infection (viral or nonviral pathogens) or tumor formation or treatment of diseases for which IFN is of therapeutic benefit. Many methods may be used to introduce the live attenuated virus formulations to a human or animal subject to induce an immune or appropriate cytokine response. These include, but are not limited to, intranasal, intratrachial, oral, intradermal, intramuscular, intraperitoneal, intravenous and subcutaneous routes. In a preferred embodiment, the attenuated viruses of the present invention are formulated for delivery intranasally.

The specifications of application Ser. Nos. WO99/64571; WO99/64068; and WO99/64570, are each incorporated herein by reference in their entireties.

3.1. DEFINITIONS

"Isolated" or "purified" when used herein to describe a protein or biologically active portion thereof (i.e., a polypeptide, peptide or amino acid fragment), refers to a protein or biologically active portion thereof substantially free of cellular material or other contaminating proteins from the cell or tissue source from which the protein is derived, or substantially free of chemical precursors or other chemicals when chemically synthesized. A protein or biologically active portion thereof (i.e., a polypeptide, peptide or amino acid fragment) that is substantially free of cellular material includes preparations of protein having less than about 30%, 20%, 10%, or 5% (by dry weight) of heterologous protein (also referred to herein as a "contaminating protein").

In certain embodiments of the invention, a "prophylactically effective amount" is the amount of a composition of the invention that reduces the incidence of cancer, viral infection, or microbial infection, in an animal. Preferably, the incidence of cancer, viral infection, or microbial infection in an animal is reduced by at least 2.5%, at least 5%, at least 10%, at least 15%, at least 25%, at least 35%, at least 45%, at least 50%, at least 75%, at least 85%, by at least 90%, at least 95%, or at least 99% in an animal administered a composition of the invention relative to an animal or group of animals (e.g., two, three, five, ten or more animals) not administered a composition of the invention.

In certain embodiments of the invention, a "therapeutically effective amount" is the amount of a composition of the invention that reduces the severity, the duration and/or the symptoms associated with cancer, viral infection, or microbial infection, in an animal. In certain other embodiments of the invention, a "therapeutically effective amount" is the amount of a composition of the invention that results in a reduction in viral titer or microbial titer by at least 2.5%, at least 5%, at least 10%, at least 15%, at least 25%, at least 35%, at least 45%, at least 50%, at least 75%, at least 85%, by at least 90%, at least 95%, or at least 99% in an animal administered a composition of the invention relative to the viral titer or microbial titer in an animal or group of animals (e.g., two, three, five, ten or more animals) not administered a composition of the invention. In certain other embodiments, a "therapeutically effective amount" is the amount of a composition of the invention that results in a reduction of the growth or spread of cancer by at least 2.5%, at least 5%, at least 10%, at least 15%, at least 25%, at least 35%, at least 45%, at least 50%, at least 75%, at least 85%, by at least 90%, at least 95%, or at least 99% in an animal administered a composition of the invention relative to the growth or spread of cancer in an animal or group of animals (e.g., two, three, five, ten or more animals) not administered a composition of the invention.

4. DESCRIPTION OF THE FIGURES

FIG. 1. System to identify viral encoded interferon antagonists. Cells are transfected with plasmids encoding known or potential interferon-antagonists. Sixteen hours later, the cells are infected with an interferon-sensitive virus, such as delNS1 virus. Viral growth is then monitored. Effective interferon-antagonists will block interferon induction and subsequent activation of antiviral pathways. The result is enhanced viral growth.

FIG. 2. Method to enhance growth of Interferon-sensitive viruses. Cells will be transfected with a plasmid encoding an interferon-antagonist and subsequently infected with the interferon-sensitive virus. Inhibition of the interferon response by the interferon antagonist will enhance virus growth.

FIG. 3. Screening assay to identify inhibitors of interferon-antagonists. Compounds will be screened for their ability to inhibit interferon antagonists. Cells containing a reporter plasmid with an interferon-stimulated response element driven GFP (ISRE-GFP) and expressing an interferon antagonist will be infected with a virus with impaired interferon antagonist activity (e.g., delNS1). These infected cells will also be treated with different test compounds.

FIG. 3A. In the presence of a compound (compound A) which does not inhibit the interferon antagonist, interferon response is not induced. Therefore, GFP signal is not detected and growth of the virus with impaired interferon antagonist activity is detected.

Figure 3B:
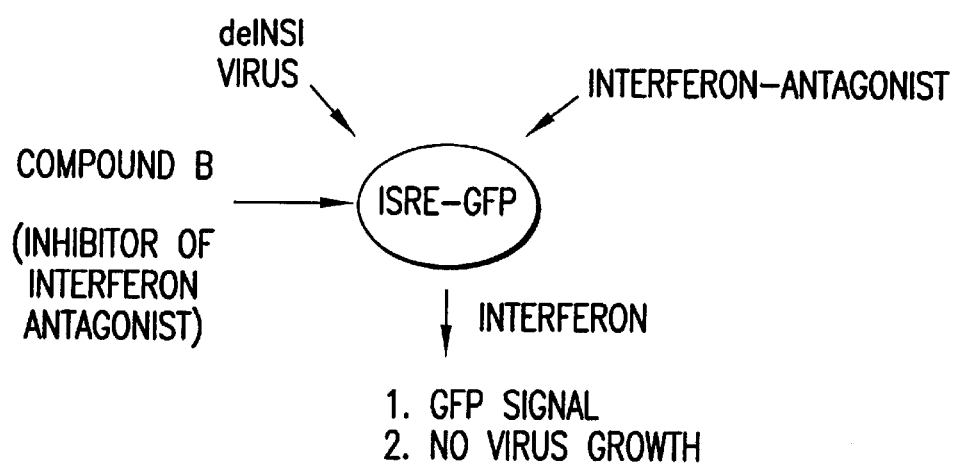

FIG. 3B. In the presence of a compound (compound B) which inhibits the interferon antagonist, interferon is produced, GFP expression is detected and growth of the virus with impaired interferon antagonist activity is not detected.

Figure 4:
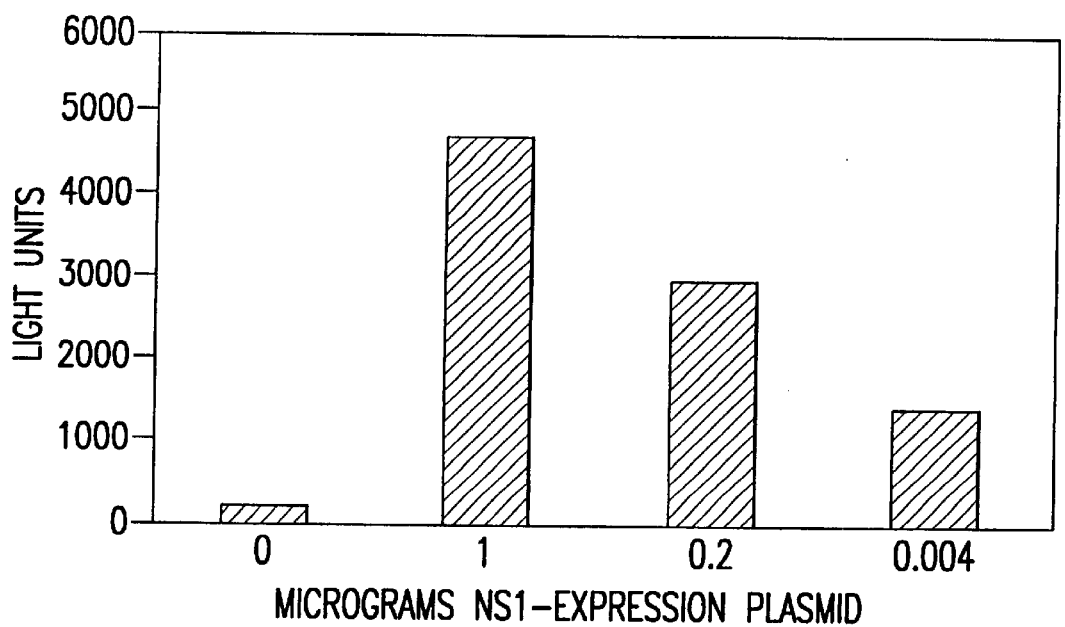

FIG. 4. Stimulation of luciferase expression from pGL2-Control by co-expression with a viral interferon antagonist. Transfection of an interferon antagonist can enhance expression of other genes. The ability to enhance expression of transfected genes may be useful when maximal gene expression is desired.

Interferon antagonists may enhance expression in vivo from gene therapy vectors.

Figure 5:
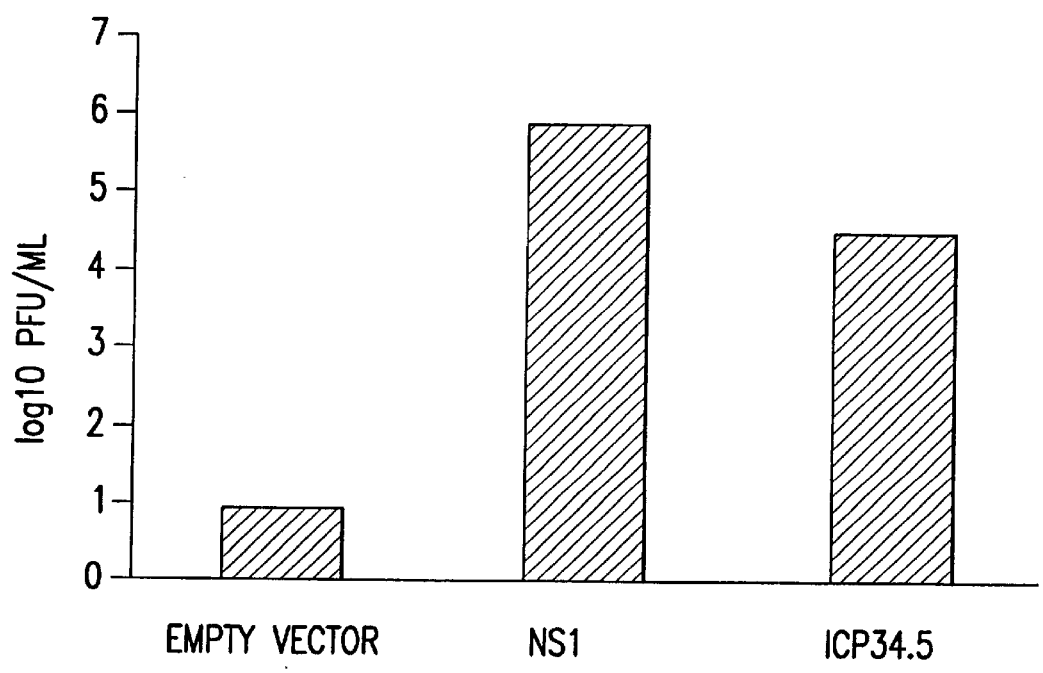

FIG. 5. Growth of the influenza delNS1 virus is complemented by transient transfection of an influenza A NS1 protein or an HSV ICP34.5 expression plasmid. MDCK cells were transfected with 4 µg of empty expression plasmid (pCAGGS), pCAGGS-PR8 NS1 SAM, or pCAGGS-134.5. Twenty-four hours later, the cells were infected with influenza delNS1 virus (moi=0.001). Forty-eight hours posttransfection, viral titers were determined by plaque assay. The results are the average of two independent experiments.

Figures 6, 7A:
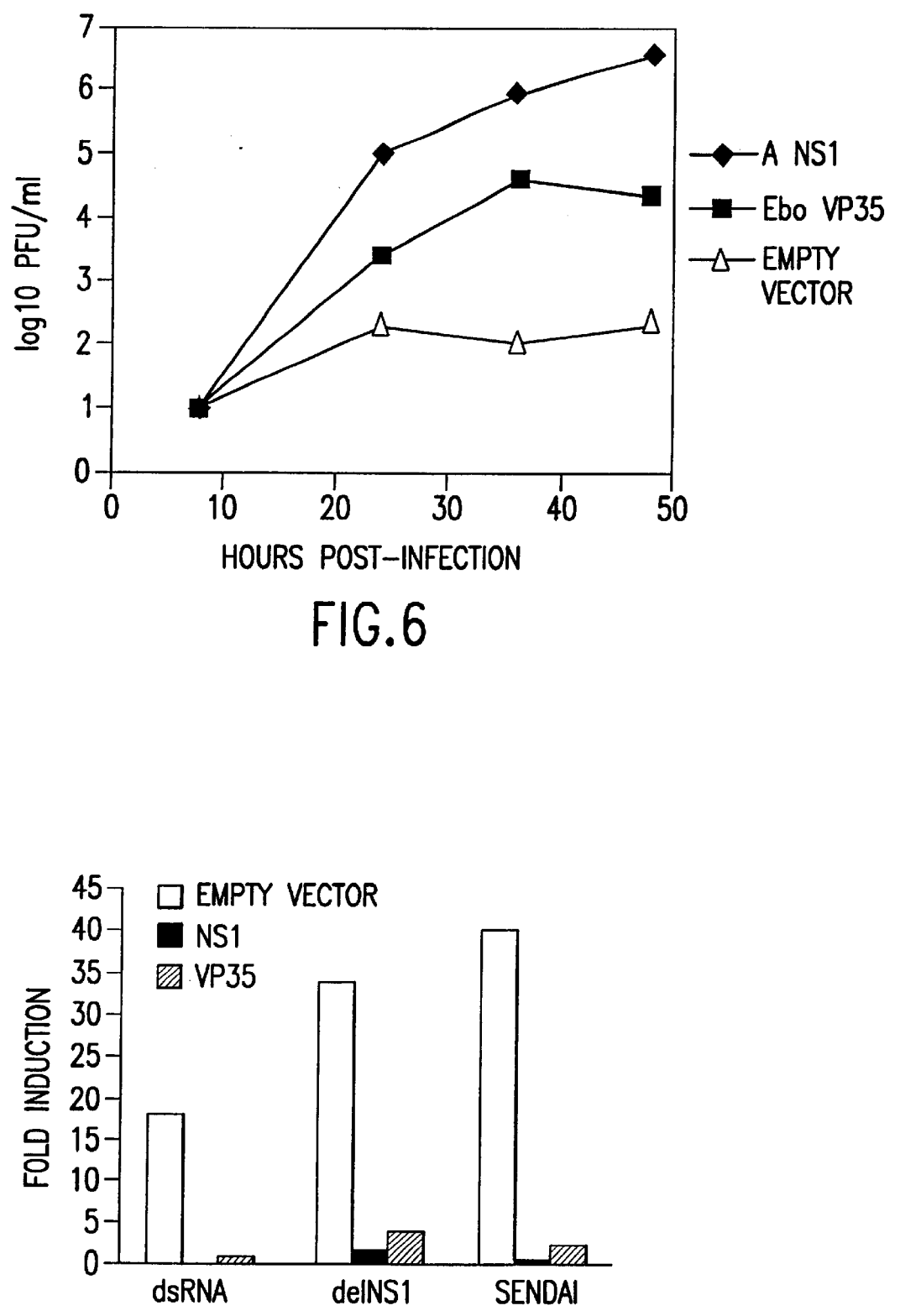

FIG. 6. Growth of the influenza delNS1 virus is complemented by the Ebola virus VP35 protein. MDCK cells were transfected with 4 µg of empty expression plasmid (pcDNA3), NS1 expression plasmid, or Ebola virus VP35 expression plasmid. Twenty-four hours later, the cells were infected with influenza delNS1 virus (moi=0.001). Viral titers were determined by plaque assay at the indicated times.

Figure 7B:
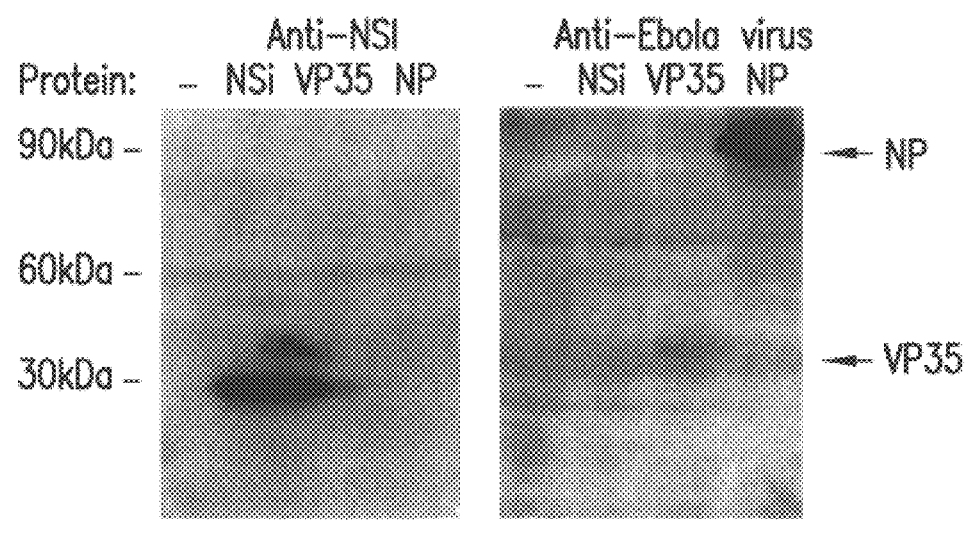

FIG. 7. Expression of Ebola virus VP35 protein inhibits dsRNA- or virus-mediated induction of an ISRE. FIG. 7A. Fold induction of an ISRE promoter-CAT reporter gene in the presence of empty vector, NS1 expression plasmid, or VP35 expression plasmid. The CAT activities were normalized to the corresponding luciferase activities to determine fold induction. FIG. 7B. Western blot showing NS1, VP35, and Ebola virus NP expression. 293 cells were transfected with 4 µg of the indicated plasmids. Forty-eight hours later, cell lysates were prepared and Western blots were performed by using the indicated antiserum.

Figures 8, 9:
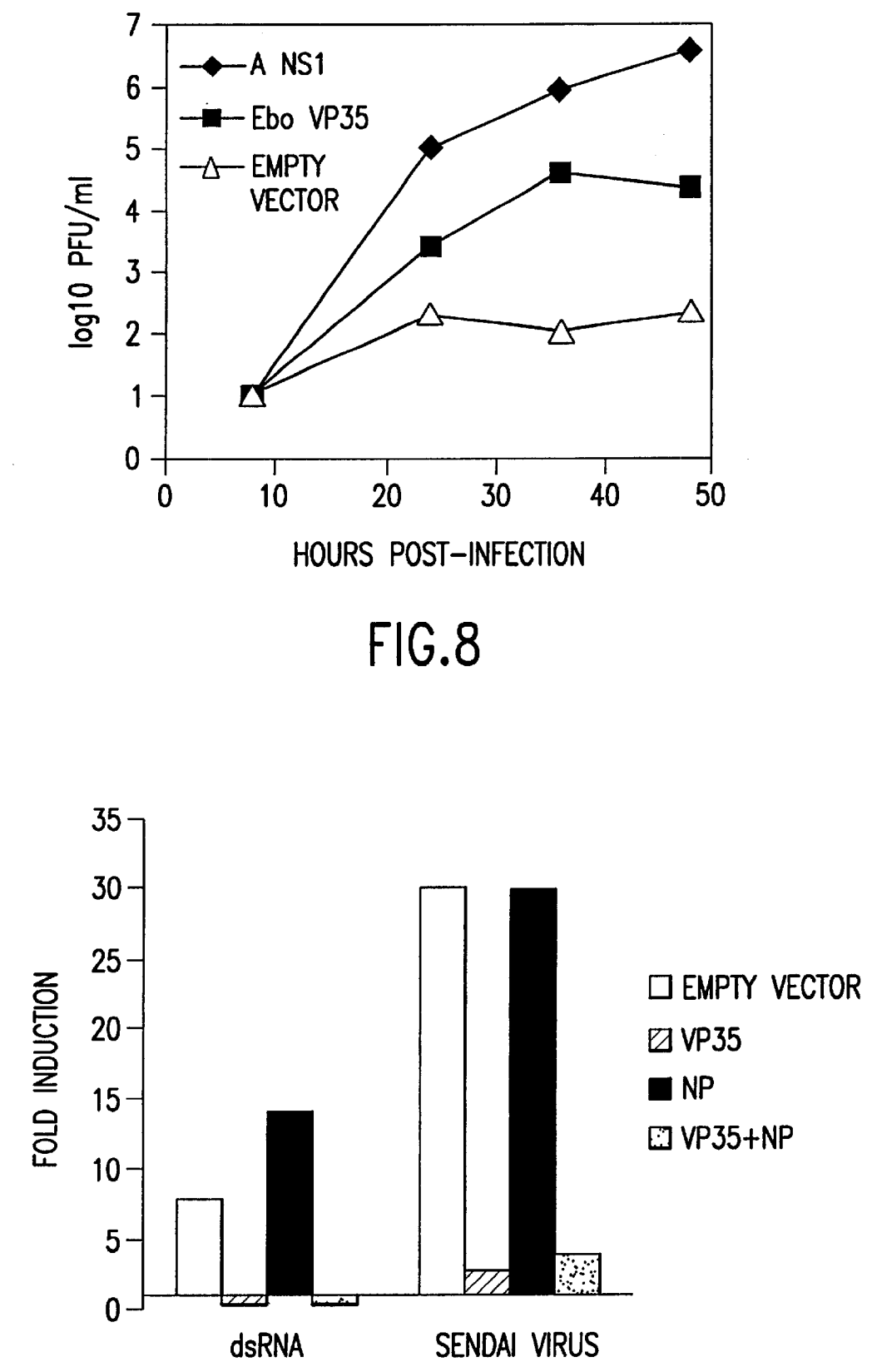

FIG. 8. The VP35 protein of Ebola virus inhibits induction of the IFN-β promoter. Inhibition of induction of the mouse IFN-β promoter. 293 cells were transfected with 4 µg of the indicated expression plasmid plus 0.3 µg each of the reporter plasmids pIFN-β-CAT and pGL2-Control. Twenty-four hours posttransfection, the cells were mock-transfected or transfected with 40 µg of polyI:polyC.

FIG. 9. The Ebola virus VP35 protein inhibits type I IFN induction when coexpressed with Ebola virus NP. Fold induction of the IFN-inducible ISRE-driven reporter in the presence of empty vector, VP35, NP, or VP35 plus NP. 293 cells were transfected with a total of 4 µg of expression plasmid, including 2 µg of a plasmid encoding an individual protein and 2 µg of a second plasmid (either empty vector or a second expression plasmid) plus 0.3 µg each of the reporter plasmids pHISG-54-CAT and pGL2-Control. Twenty-four hours posttransfection, the cells were mock-treated or treated with the indicated IFN inducer. Twenty-four hours postinduction, CAT and luciferase assays were performed. The CAT activities were normalized to the corresponding luciferase activities to determine fold induction.

5. DETAILED DESCRIPTION OF INVENTION

The invention relates to screening assays to identify viral proteins with interferon antagonizing function. The present invention relates to identifying viral proteins that have the ability to complement replication of an attenuated virus with impaired ability to antagonize cellular interferon responses. The present invention also relates to screening assays to identify anti-viral agents which inhibit interferon antagonist activity and inhibit viral replication.

The screening assays of the invention are based, in part, on Applicants' discovery that viral proteins such as influenza NS1, ebola virus VP35 and respiratory syncytial virus NS2 function as an IFN antagonists, in that these proteins inhibit the IFN mediated response of virus-infected cells. However, the principles can be analogously applied and extrapolated to other viruses, including other segmented and non-segmented RNA viruses, such viruses may include, but are not limited to paramyxoviruses (Sendai virus, parainfluenza virus, mumps, Newcastle disease virus), morbillivirus (measles virus, canine distemper virus and rinderpest virus); pneumovirus (respiratory syncytial virus and bovine respiratory virus); rhabdovirus (vesicular stomatitis virus and lyssavirus); RNA viruses, including Hepatitis C virus and retroviruses, lentiviruses, including human immunodeficiency virus (HIV), and DNA viruses, including vaccinia, adenoviruses, adeno-associated virus, hepadna viruses, herpes viruses and poxviruses.

The present invention relates to in vitro and cell based assays to identify viral proteins with interferon antagonizing function. In a preferred embodiment, the present invention relates to transfection-based assays to identify viral proteins with interferon-antagonizing activities. In one embodiment, the transfection-based assays of the invention encompass expressing the putative interferon antagonist in a cell infected with a virus with impaired ability to antagonize cellular interferon functions. Interferon antagonist activity may be determined by the ability of the viral protein to complement replication of the impaired virus. The ability of an interferon antagonist to complement replication of an impaired virus, i.e., a virus in which the interferon antagonist activity is mutated or reduced, may be determined in a cell based or animal based assay. In either assay system, the ability of the interferon antagonist to complement the impaired virus is determined by an increase or an enhancement in viral replication of viral load.

In accordance with the screening assays of the present invention, numerous in vitro and cell based assays may be used to identify viral proteins with interferon antagonist activity. Interferon antagonist activities may be determined by the ability of a viral protein to inhibit or reduce any known interferon based activity, including regulation of interferon expression, regulation of interferon regulated promoter elements and genes, regulation of signal transduction pathways, such as the phosphorylation of Janus Kinases (JAKS) and signal transduction activator of transcription (STATS).

The present invention relates to screening methods to identify potential antiviral agents that target interferon antagonists. The present invention relates to screening assays based on identifying agents which inhibit interferon antagonizing activity. The antiviral screening assays of the invention encompass in vitro, in vivo and animal models for identifying antiviral agents that target interferon antagonists.

The ability of an agent or compound to target or modulate a viral interferon antagonist may be determined by measuring the ability of said agent or compound to modulate or regulate, either directly or indirectly, the viral protein's inhibition of cellular interferon responses. The invention encompasses screening for an agent or compound with the ability to target or modulate viral interferon antagonist activities, including the ability of a viral protein to inhibit or reduce any known interferon based activity, including regulation of interferon expression, regulation of interferon regulated promoter elements and genes, regulation of signal transduction pathways, such as the phosphorylation of Janus Kinases (JAKS) and signal transduction activator of transcription (STATS).

The present invention also provides cell and animal based models for the identification of an agent or compound to target or modulate a viral interferon antagonist and inhibit or reduce viral replication. The cell and animal based model of the invention comprising measuring the ability of a test agent or compound to inhibit the complementation of a virus with impaired interferon antagonist activity by a viral interferon antagonist.

In such an assay system, the interferon antagonist may be provided to the virus with impaired interferon antagonistic in trans or in cis. An interferon antagonist may be provided to the cell or animal system in trans by providing the nucleic acids encoding said interferon antagonist or the interferon antagonist polypeptide using standard techniques known to those of skill in the art. An interferon antagonist may be provided in cis by constructing a chimeric virus comprising a nucleic acid encoding said interferon antagonist and nucleic acids encoding the virus with impaired interferon antagonist activity.

In accordance with the present invention, the identified viral interferon antagonists can be used for several applications. Viral interferon antagonists can be used as targets for mutagenesis aimed at creating viruses with impaired interferon antagonist activity and attenuated phenotypes. Viral interferon antagonists can be used to enhance growth of viruses that display restricted growth on interferon producing substrates. Such growth substrates may allow the isolation and characterization of interferon sensitive viruses and may increase viral titers obtained in tissue culture. Viral interferon antagonists may be used to enhance translation of co-expressed genes. This capability may be useful in maximizing expression of transfected genes. Viral interferon antagonists may be used to facilitate gene therapy or DNA vaccination by increasing and/or prolonging gene expression in the presence of interferon.

The present invention also encompasses pharmaceutical compositions comprising antiviral agents which inhibit viral interferon antagonist activity and methods of administering such pharmaceutical compositions for the treatment and prevention of viral replication.

5.1. Screening Assays For Identifying Viral Proteins Having Interferon Antagonist Activity The present invention relates to screening methods to identify viral proteins with interferon antagonizing function. The screening assays of the invention encompass in vitro and in vivo approaches to assay for the ability of a viral protein to antagonize cellular interferon responses. In accordance with the present invention, interferon antagonist activities may be determined by the ability of a viral protein to inhibit or reduce any known interferon based activity, as compared to the absence of the viral protein. Interferon based activities which may be assayed include, but are not limited to, regulation of interferon regulated promoter elements and genes, regulation of reporter genes, increase in translation of proteins, and regulation of signal transduction pathways, such as the phosphorylation of JAKS and STATS.

In a preferred embodiment, the present invention relates to a complementation assay. A complementation assay allows for the screening of a viral protein to determine if it possesses an interferon antagonist activity thereby complementing the growth of a virus lacking said activity.

A complementation assay consists of using an appropriate cell line that is susceptible to the virus from which the virus with impaired interferon antagonist activity is derived. The assay comprises determining the ability of a viral protein to complement the interferon antagonist function and allow the virus to replicate and grow. Any viral protein may be assayed for interferon antagonist activity.

Increased viral replication in the presence of the viral protein or peptide, compared to the absence of said protein or peptide, indicates the viral protein or peptide has interferon antagonist activity.

In accordance with the present invention, the screening assays to identify viral interferon antagonists may be performed in any appropriate in vitro assay system, cell extract or cell, including primary cells and cell lines.

The viral protein to be tested for interferon antagonist activity can be obtained from any virus. These proteins include, for example, NS1 and other analogous proteins originating from various types of viruses. Such viruses may include, but are not limited to paramyxoviruses (Sendai virus, parainfluenza virus, mumps, Newcastle disease virus), morbilliviruses (measles virus, canine distemper virus and rinderpest virus); pneumoviruses (respiratory syncytial virus and bovine respiratory virus); rhabdoviruses (vesicular stomatitis virus and lyssavirus); RNA viruses, including hepatitis C virus and retroviruses, and DNA viruses, including vaccinia, adenoviruses, hepadna viruses, herpes viruses and poxviruses.

In accordance with the present invention, the viral proteins to be tested for interferon antagonist activity may be provided to the assay system to be used as an isolated protein or fragment thereof or in another embodiment, the nucleic acids encoding the viral protein or a portion thereof may be provided to the assay system.

Viral proteins to be tested for interferon antagonist activity may be isolated or purified from a virus or viral extract using standard techniques known to those of skill in the art. In another embodiment the viral protein to be tested may be expressed recombinantly using standard techniques known to those of skill in the art. Nucleic acids encoding viral proteins to be tested for interferon antagonist activity may be supplied using standard techniques known to those of skill in the art. Nucleic acids encoding viral proteins to be tested should be operatively linked to the appropriate regulatory elements to allow for their expression. Such nucleic acids may be supplied by way of plasmid, viral vector, bacteriophage etc. and may be operatively linked to regulatory elements selected from viral promoter elements, inducible promoters, constitutive promoters etc.

The ability of a viral protein to antagonize interferon responses is determined by the ability of the viral protein to reduce or inhibit the interferon response being assayed, as compared to the absence of the viral protein.

5.1.1. Complementation Assays

In a preferred embodiment, the present invention encompasses screening assays to identify viral interferon antagonists based on the ability of the viral protein to complement the growth and replication of a virus with impaired interferon antagonist activity, as compared to the absence of the viral protein.

In accordance with the embodiment of the invention, the viral protein to be tested for its ability to complement the growth and replication of a virus with impaired interferon antagonist activity is provided to the impaired virus in trans. The viral protein or nucleic acids encoding the viral protein, and the impaired virus is provided as a packaged virion or the nucleic acids encoding the impaired virus are provided to the cell. In such an embodiment, the cell may be engineered to express the components of the assay using standard techniques available to those skilled in the art. In such an embodiment, the growth and replication of the virus is compared in the presence and the absence of the viral protein.

In a preferred embodiment the viral protein to be tested for its ability to complement the growth and replication of a virus with impaired interferon antagonist activity is provided to the impaired virus in cis. In such an embodiment, a chimeric virus is engineered so that the chimeric virus expresses the viral protein to be tested. In such an embodiment, the growth and replication of the impaired virus is compared to that of the chimeric virus.

In a preferred embodiment the virus with impaired interferon antagonist activity is influenza delNS1, however, any virus with impaired interferon antagonist activity can be used in accordance with the invention.

The present invention encompasses chimeric viruses wherein the virus has a defect such that it is impaired in its interferon antagonist activity and said defect is complemented by the presence of a heterologous interferon antagonist. The chimeric virus can be made using any RNA virus including negative strand RNA virus that are either segmented or non-segmented. In a preferred embodiment the chimeric virus is engineered using an influenza virus.

"Reverse genetics" techniques are used to construct recombinant and/or chimeric influenza virus templates engineered to direct the expression of heterologous gene products. When combined with purified viral RNA-directed RNA polymerase, these virus templates are infectious, replicate in hosts, and their heterologous gene is expressed and packaged by the resulting recombinant influenza viruses (For a description of the reverse genetics approach see Palese et al., U.S. Pat. No. 5,166,057 and Palese, WO93/21306, each of which is incorporated by reference herein in its entirety). The expression products and/or chimeric virions obtained can be used in vaccine formulations, and the strain variability of the influenza virus permits construction of a vast repertoire of vaccine formulations and obviates the problem of host resistance.

The use of reverse genetics to genetically engineer influenza viruses, including attenuated influenza viruses, and methods for their production, are described in Palese et al. (U.S. Pat. No. 5,166,057) and Palese (WO93/21306). Such reverse genetics techniques can be utilized to engineer a mutation, including but not limited to an insertion, deletion, or substitution of an amino acid residue(s), an antigen(s), or an epitope(s) into a coding region of the viral genome so that altered or chimeric viral proteins are expressed by the engineered virus. Alternatively, the virus can be engineered to express the interferon antagonist as an independent polypeptide.

The reverse genetics technique involves the preparation of synthetic recombinant viral RNAs that contain the non-coding regions of the negative strand virus which are essential for the recognition of viral RNA by viral polymerases and for the packaging into mature virions. The recombinant RNAs are synthesized from a recombinant DNA template and reconstituted in vitro with purified viral polymerase and nucleoprotein complex to form recombinant ribonucleoproteins (RNPs) which can be used to transfect cells.

Preferably, the viral polymerase proteins are present during in vitro transcription of the synthetic RNAs prior to transfection. The synthetic recombinant RNPs can be rescued into infectious virus particles. The foregoing techniques are described in Palese et al., U.S. Pat. No. 5,166,057, and in Enami and Palese, 1991, J. Virol. 65:2711–2713, each of which is incorporated by reference herein in its entirety.

Such reverse genetics techniques can be used to insert an interferon antagonist into an influenza virus protein so that a chimeric protein is expressed by the virus. Any of the influenza viral proteins may be engineered in this way.

Alternatively, viral genes can be engineered to encode a viral protein and the interferon antagonist as independent polypeptides. To this end, reverse genetics can advantageously be used to engineer a bicistronic RNA segment as described in U.S. Pat. No. 5,166,057, which is incorporated by reference in its entirety herein; i.e., so that the engineered viral RNA species directs the production of both the viral protein and the interferon antagonist as independent polypeptides.

Attenuated strains of influenza may be used as the "parental" strain to generate the influenza recombinants. Alternatively, reverse genetics can be used to engineer both the attenuation characteristics as well as the interferon antagonist into the recombinant influenza viruses of the invention.

5.1.2 Interferon Activities to be Assayed

The screening methods of the invention also encompass identifying those viral proteins which antagonize IFN responses. In accordance with the screening methods of the invention, induction of IFN responses may be measured bye assaying levels of IFN expression or expression of target genes or reporter genes induced by IFN following transfection with the viral protein or activation of transactivators involved in the IFN expression and/or the IFN response. Interferon antagonist activity can also be determined by monitoring gene expression. This would include endogenously expressed genes that are up regulated in response to interferon or increased expression of a reporter gene linked to an interferon responsive element (FIGS. 1 and 2).

In yet another embodiment of the selection systems of the invention, induction of IFN responses may be determined by measuring the phosphorylated state of components of the IFN pathway following transfection with the test viral protein, e.g., IRF-3, which is phosphorylated in response to double-stranded RNA. In response to type I IFN, Jak1 kinase and TyK2 kinase, subunits of the IFN receptor, STAT1, and STAT2 are rapidly tyrosine phosphorylated. Thus, in order to determine whether the viral protein induces IFN responses, cells, such as 293 cells, are transfected with the test viral protein and following transfection, the cells are lysed. IFN pathway components, such as Jak1 kinase or TyK2 kinase, are immunoprecipitated from the infected cell lysates, using specific polyclonal sera or antibodies, and the tyrosine phosphorylated state of the kinase is determined by immunoblot assays with an anti-phosphotyrosine antibody (e.g., see Krishnan et al. 1997, Eur. J. Biochem. 247:298–305). An enhanced phosphorylated state of any of the components of the IFN pathway following transfection with the viral protein would indicate induction of IFN responses by the viral protein.

In yet another embodiment, the screening systems of the invention encompass measuring the ability to bind specific DNA sequences or the translocation of transcription factors induced in response to transfection of a viral protein, e.g., IRF3, STAT1, STAT2, etc. In particular, STAT1 and STAT2 are phosphorylated and translocated from the cytoplasm to the nucleus in response to type I IFN. The ability to bind specific DNA sequences or the translocation of transcription factors can be measured by techniques known to those of skill in the art, e.g., electromobility gel shift assays, cell staining, etc.

In yet another embodiment of the screening systems of the invention, induction of IFN responses may be determined by measuring IFN-dependent transcriptional activation following transfection with the test viral protein. In this embodiment, the expression of genes known to be induced by IFN, e.g., Mx, PKR, 2-5-oligoadenylatesynthetase, major histocompatibility complex (MHC) class I, etc., can be analyzed by techniques known to those of skill in the art (e.g., northern blots, western blots, PCR, etc.).

Alternatively, test cells such as human embryonic kidney cells or human osteogenic sarcoma cells, are engineered to transiently or constitutively express reporter genes such as luciferase reporter gene or chloramphenicol transferase (CAT) reporter gene under the control of an interferon stimulated response element, such as the IFN-stimulated promoter of the ISG-54K gene (Bluyssen et al., 1994, Eur. J. Biochem. 220:395–402). Cells are transfected with the viral protein and the level of expression of the reporter gene compared to that in untransfected cells or cells transfected with a plasmid lacking a test protein, or alternatively containing a viral protein known not to have interferon antagonist activity. An increase in the level of expression of the reporter gene following transfection with the viral protein would indicate that the viral protein is inducing an IFN response.

In a preferred embodiment the virus with impaired interferon antagonist activity is the influenza A virus mutant delNS1 and the test protein can be any viral protein. Interferon antagonist activity can be monitored by any of the methods described above including but not limited to the ability of the viral protein to enhance viral replication; the ability of the viral protein to enhance interferon regulated gene expression; or the ability of the viral protein to enhance signal transduction in pathways induced by interferon activation.

In yet another preferred embodiment the virus is a chimeric mutant virus comprised of a heterologous viral protein of interest and a mutation that impairs the native interferon antagonist activity. Interferon antagonist activity can be monitored by any of the methods described above including but not limited to the ability of the viral protein to enhance viral replication; the ability of the viral protein to enhance interferon regulated gene expression; or the ability of the viral protein to enhance signal transduction in pathways induced by interferon activation.

5.1.3. In Vivo Screening Assays for Identifying Viral Proteins Having Interferon Antagonist Activity The screening assay can be performed in any appropriate animal model. An appropriate animal model would be one that is susceptible to infection with the virus from which the virus with impaired interferon antagonist activity is derived. The animal model may be any animal, preferably the animal is a mouse, rat, rabbit or avian.

The complement assays of the present invention as described in Section 5.1.1 may be applied to in vivo screening assays. The viral protein to be tested could be administered to the animal in trans to the impaired virus or in cis, such as a chimeric virus. If the viral protein to be tested is to be provided in trans, the nucleic acid encoding the viral protein to be tested in the form of a plasmid, or viral vector. The viral protein to be tested could be provided to the animal model as a protein or peptide.

In addition to the introduction of the viral protein to be tested, the animal would also be infected with a virus with impaired interferon antagonist activity. In a preferred embodiment of the invention, the virus with impaired interferon antagonist activity is influenza A virus delNS1.

The test animal can be monitored for viral titer, or gene expression of genes endogenously regulated by interferon or an exogenous gene under the control of an interferon response element using any method known in the art.

As an example, but not as a limitation, a plaque assay or quantitative PCR could be used. The growth and replication of the virus with impaired interferon activity can be compared in the presence and absence of the viral protein to be tested.

In another embodiment the virus administered to the test animal can be any virus with an impaired interferon activity and the protein of interest can be any viral protein, the growth and replication of the virus in the presence of the viral protein is compared to that in the absence of the viral protein.

The test animal can be monitored for viral titer, or gene expression of genes endogenously regulated by interferon or an exogenous gene under the control of an interferon response element using any method known in the art. As an example, but not as a limitation, a plaque assay or quantitative PCR could be used. Alternatively, the animal can be monitored for susceptibility to other infections.

In another preferred embodiment the virus is a chimeric virus with an impaired interferon antagonist activity and an exogenous protein with potential interferon antagonist activity. As a control additional animals could receive a non-chimeric attenuated virus with impaired interferon antagonist activity.

The test animal can be monitored for viral titer. An increase in viral titer over that obtained with a control protein or peptide, or no protein or peptide, would signify that the test protein possessed interferon antagonist activity. Alternatively, gene expression of genes endogenously regulated by interferon or an exogenous gene under the control of an interferon response element. An increase in gene expression would signify that the test protein possessed interferon antagonist activity. The animal can also be monitored for susceptibility to other infections. An increase in susceptibility to other infections would indicate that the test protein possessed interferon antagonist activity.

The screening methods of the invention also encompass identifying those viral proteins which antagonize IFN responses. In accordance with the screeening methods of the invention, induction of IFN responses may be measured by assaying levels of IFN expression or expression of target genes or reporter genes induced by IFN following transfection with the viral protein or activation of transactivators involved in the IFN expression and/or the IFN response.

In yet another embodiment of the selection systems of the invention, induction of IFN responses may be determined by measuring the phosphorylated state of components of the IFN pathway following transfection with the test viral protein, e.g., IRF-3, which is phosphorylated in response to double-stranded RNA. In response to type I IFN, Jak1 kinase and TyK2 kinase, subunits of the IFN receptor, STAT1, and STAT2 are rapidly tyrosine phosphorylated. Thus, in order to determine whether the viral protein induces IFN responses, cells, such as 293 cells, are transfected with the test viral protein and following transfection, the cells are lysed. IFN pathway components, such as Jak1 kinase or TyK2 kinase, are immunoprecipitated from the infected cell lysates, using specific polyclonal sera or antibodies, and the tyrosine phosphorylated state of the kinase is determined by immunoblot assays with an anti-phosphotyrosine antibody (e.g., see Krishnan et al. 1997, Eur. J. Biochem. 247: 298–305). An enhanced phosphorylated state of any of the components of the IFN pathway following transfection with the viral protein would indicate induction of IFN responses by the viral protein.

In yet another embodiment, the screening systems of the invention encompass measuring the ability to bind specific DNA sequences or the translocation of transcription factors induced in response to transfection of a viral protein, e.g., IRF3, STAT1, STAT2, etc. In particular, STAT1 and STAT2 are phosphorylated and translocated from the cytoplasm to the nucleus in response to type I IFN. The ability to bind specific DNA sequences or the translocation of transcription factors can be measured by techniques known to those of skill in the art, e.g., electromobility gel shift assays, cell staining, etc.

In yet another embodiment of the screening systems of the invention, induction of IFN responses may be determined by measuring IFN-dependent transcriptional activation following transfection with the test viral protein. In this embodiment, the expression of genes known to be induced by IFN, e.g., Mx, PKR, 2-5-oligoadenylatesynthetase, major histocompatibility complex (MHC) class I, etc., can be analyzed by techniques known to those of skill in the art (e.g., northern blots, western blots, PCR, etc.). Alternatively, test cells such as human embryonic kidney cells or human osteogenic sarcoma cells, are engineered to transiently or constitutively express reporter genes such as luciferase reporter gene or chloramphenicol transferase (CAT) reporter gene under the control of an interferon stimulated response element, such as the IFN-stimulated promoter of the ISG-54K gene (Bluyssen et al., 1994, Eur. J. Biochem. 220:395–402). Cells are transfected with the test viral protein and the level of expression of the reporter gene compared to that in untransfected cells or cells transfected with a plasmid lacking a test protein, or alternatively containing a protein known not to have interferon antagonist activity. An increase in the level of expression of the reporter gene following transfection with the test viral protein would indicate that the test viral protein is inducing an IFN response.

5.2. Screening Assays for Identifying Antiviral Agents that Target Viral Interferon Antagonists The present invention includes methods for screening agents to determine if the agent inhibits or reduces interferon antagonist activity.

The assay utilizes viruses with an impaired interferon antagonist activity, a plasmid encoding a viral interferon antagonist and a test agent. The assay determines if the test agent inhibits or reduces interferon antagonist activity (FIG. 3).

Any compound can be screened in connection with the anti-viral assays of the present invention, such compounds include, but are not limited to, proteins, polypeptides, peptides, nucleic acids, including dominant negative mutants, antisense, ribozyme or triple helix molecules, antibodies, small organic molecules, inorganic molecules. In addition, any known antiviral compound can be screened for the ability to inhibit interferon antagonist activity.

5.2.1. In Vitro Screening Assays for Identifying Antiviral Agents that Target Viral Interferon Antagonists The present invention encompasses screening assays that identify antiviral agents that target a viral interferon antagonist. The present invention encompasses screening assays to identify antiviral agents that modulate the ability of an interferon antagonist to complement the growth and replication of a virus with impaired interferon antagonist activity. The assay can be performed in any suitable cell that is susceptible to the virus with impaired interferon antagonist activity.

In accordance with the present invention, the virus with impaired interferon antagonist activity and the interferon antagonist need not be obtained from the same virus. In a preferred embodiment, the virus from which the virus with impaired interferon antagonist activity is derived, is selected based on its ability to infect many types of hosts.

An example of such a virus is influenza virus and an example of such a virus with impaired interferon antagonist activity is delNS1.

Any cell which is susceptible to the virus from which the virus with impaired interferon activity is derived can be used. Cells may be selected from primary cell cultures, immortalized cells and cell lines.

In accordance with the screening assays of the invention, a test agent may be assayed for its ability to inhibit or modulate the ability of an interferon antagonist to complement the replication and growth of a virus with impaired interferon antagonist activity when provided in trans.

In such an embodiment the interferon antagonist may be introduced into the cell or cell extract.

In another embodiment, the nucleic acids encoding the interferon antagonist may be introduced into the cell. In such an embodiment, the cell may be engineered using standard techniques available to those of skill in the art to express the interferon antagonist transiently, under inducible conditions or constitutively.

In accordance with the screening assay of the invention, the virus with impaired interferon antagonist activity may be introduced to the cell or extract as a packaged virion. In yet another embodiment the nucleic acids encoding the virus with impaired interferon antagonist activity may be introduced into the cell. In such an embodiment, the cell may be engineered using standard techniques available to those of skill in the art to express the nucleic acids encoding the impaired virus transiently, under inducible conditions or constitutively.

In accordance with the present invention, the interferon antagonist and the impaired virus may be provided consecutively or concurrently in the presence and absence of a test agent. The screening assays of the present invention are not be limited by the order in which the components of the assay are provided to the cell.

In yet another embodiment of the invention, a test agent may be assayed for its ability to inhibit or modulate the ability of an interferon antagonist to complement the replication and growth of a virus with impaired interferon antagonist activity when provided in cis. In such an embodiment, a chimeric virus is engineered, such that the interferon antagonist is engineered so that it provides interferon antagonist function to a virus that is impaired in this function. The chimeric virus is provided to a cell susceptible to infection by the virus from which the impaired virus is derived. The chimeric virus is provided to the cell in the presence or absence of the test agent.

Titers are monitored and compared between the treated cells and the untreated cells, by any method known in the art. Viral titers may be measured using any technique known to those of skill in the art.

For example, but not as a limitation titers can be determined by plaque assay. A lower viral titer in the presence of the test agent as compared to the absence, would indicate that the test agent possessed anti-interferon antagonist activity and would be a suitable anti-viral drug candidate.

In a preferred embodiment the virus is influenza virus delNS1. The interferon antagonist can be any known interferon antagonist, for example, but not as a limitation, NS1 of influenza virus and the test agent can be any compound believed to have anti interferon antagonist activity.

In another embodiment the virus is any virus known to be lacking interferon antagonist activity. The interferon antagonist can be any viral interferon antagonist, known or identified by the screening assays of the present invention, for example, but not as a limitation, NS1 of influenza virus and the test agent can be any compound believed to have anti interferon antagonist activity.

5.2.2. In Vivo Screening Assays for Identifying Antiviral Agents that Target Viral Interferon Antagonists The present invention encompasses screening assays that identify antiviral agents that target a viral interferon antagonist. The present invention encompasses screening assays to identify antiviral agents that modulate the ability of an interferon antagonist to complement the growth and replication of a virus with impaired interferon antagonist activity. The assay can be performed in any suitable animal that is susceptible to the virus with impaired interferon antagonist activity.

In accordance with the present invention, the virus with impaired interferon antagonist activity and the interferon antagonist need not be obtained from the same virus. In a preferred embodiment, the virus from which the virus with impaired interferon antagonist activity is derived, is selected based on its ability to infect many types of hosts. An example of such a virus is influenza virus and an example of such a virus with impaired interferon antagonist activity is delNS1.

Any animal which is susceptible to the virus from which the virus with impaired interferon activity is derived can be used. As an example, but not as a limitation, avians, monkeys, rats mice, dogs, rabbits, or pigs may be used.

In accordance with the screening assays of the invention, a test agent may be assayed for its ability to inhibit or modulate the ability of an interferon antagonist to complement the replication and growth of a virus with impaired interferon antagonist activity when provided in trans. In such an embodiment the interferon antagonist may be introduced into the animal. In another embodiment, the nucleic acids encoding the interferon antagonist may be introduced into the animal. In such an embodiment, the animal may be engineered using standard techniques available to those of skill in the art to express the interferon antagonist transiently, under inducible conditions or constitutively.

In accordance with the screening assay of the invention, the virus with impaired interferon antagonist activity may be introduced to the animal as a packaged virion. In yet another embodiment the nucleic acids encoding the virus with impaired interferon antagonist activity may be introduced into the animal. In such an embodiment, the cell may be engineered using standard techniques available to those of skill in the art to express the nucleic acids encoding the impaired virus transiently, under inducible conditions or constitutively.

In accordance with the present invention, the interferon antagonist and the impaired virus may be provided consecutively or concurrently in the presence and absence of a test agent. The screening assays of the present invention are not be limited by the order in which the components of the assay are provided to the animal.

In yet another embodiment of the invention, a test agent may be assayed for its ability to inhibit or modulate the ability of an interferon antagonist to complement the replication and growth of a virus with impaired interferon antagonist activity when provided in cis. In such an embodiment, a chimeric virus is engineered, such that the interferon antagonist is engineered so that it provides interferon antagonist function to a virus that is impaired in this function.

The chimeric virus is provided to an animal susceptible to infection by the virus from which the impaired virus is derived. The chimeric virus is provided to the animal in the presence or absence of the test agent.

Titers are monitored and compared between the treated animals and the untreated animals, by any method known in the art. Viral titers may be measured using any technique known to those of skill in the art. For example, but not as a limitation titers can be determined by plaque assay. A lower viral titer in the presence of the test agent as compared to its absence, would indicate that the test agent possessed anti-interferon antagonist activity and would be a suitable antiviral drug candidate.

In another embodiment the virus is any virus known to be lacking interferon antagonist activity. The interferon antagonist can be any viral interferon antagonist, known or identified by the screening assays of the present invention, for example, but not as a limitation, NS1 of influenza virus and the test agent can be any compound believed to have anti interferon antagonist activity.

5.3. Viruses With Impaired Interferon Antagonist Activity

The screening assays of the invention can be used to identify viral proteins with interferon antagonist activity. Once such a viral protein has been identified, the protein, the nucleic acid encoding the protein and the elements regulating the expression of the protein can be the target of manipulation and/or mutation to create a virus with impaired interferon antagonist activity.

Viruses with impaired interferon antagonist activity can include naturally occurring mutants with impaired interferon antagonist activity, engineered mutants with impaired interferon antagonist activity and recombinant viruses with impaired interferon antagonist activity.

Any mutant virus or strain which has a decreased IFN antagonist activity can be selected and used in accordance with the invention. In one embodiment, naturally occurring mutants or variants, or spontaneous mutants can be selected that have an impaired ability to antagonize the cellular IFN response. In another embodiment, mutant viruses can be generated by exposing the virus to mutagens, such as ultraviolet irradiation or chemical mutagens, or by multiple passages and/or passage in non-permissive hosts. Screening in a differential growth system can be used to select for those mutants having impaired IFN antagonist function. For viruses with segmented genomes, the attenuated phenotype can be transferred to another strain having a desired antigen by reassortment, (i.e., by coinfection of the attenuated virus and the desired strain, and selection for reassortants displaying both phenotypes).

In another embodiment, mutations can be engineered into a negative strand RNA virus such as influenza, RSV, NDV, VSV and PIV, using "reverse genetics" approaches. In this way, natural or other mutations which confer the attenuated phenotype can be engineered into vaccine strains. For example, deletions, insertions or substitutions of the coding region of the gene responsible for IFN antagonist activity (such as the NS1 of influenza) can be engineered. Deletions, substitutions or insertions in the non-coding region of the gene responsible for IFN antagonist activity are also contemplated. To this end, mutations in the signals responsible for the transcription, replication, polyadenylation and/or packaging of the gene responsible or the IFN-antagonist activity can be engineered. For example, in influenza, such modifications can include but are not limited to: substitution of the non-coding regions of an influenza A virus gene by the non-coding regions of an influenza B virus gene (Muster, et al., 1991, Proc. Natl. Acad. Sci. USA, 88:5177), base pairs exchanges in the non-coding regions of an influenza virus gene (Fodor, et al., 1998, J Virol. 72:6283), mutations in the promoter region of an influenza virus gene (Piccone, et al., 1993, Virus Res. 28:99; Li, et al., 1992, J Virol. 66:4331), substitutions and deletions in the stretch of uridine residues at the 5' end of an influenza virus gene affecting polyadenylation (Luo, et al., 1991, J Virol. 65:2861; Li, et al., J Virol. 1994, 68(2):1245–9). Such mutations, for example to the promoter, could down-regulate the expression of the gene responsible for IFN antagonist activity. Mutations in viral genes which may regulate the expression of the gene responsible for IFN antagonist activity are also within the scope of viruses that can be used in accordance with the invention.

The present invention also relates to mutations to the NS1 gene segment that may not result in an altered IFN antagonist activity or an IFN-inducing phenotype but rather results in altered viral functions and an attenuated phenotype e.g., altered inhibition of nuclear export of poly(A)-containing mRNA, altered inhibition of pre-mRNA splicing, altered inhibition of the activation of PKR by sequestering of dsRNA, altered effect on translation of viral RNA and altered inhibition of polyadenylation of host mRNA (e.g., see Krug in Textbook of Influenza, Nicholson et al. Ed. 1998, 82–92, and references cited therein).

The reverse genetics technique involves the preparation of synthetic recombinant viral RNAs that contain the non-coding regions of the negative strand virus RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. Pat. No. 6,146,642; in International Patent Publications PCT WO97/12032 published Apr. 3, 1997; WO96/34625 published Nov. 7, 1996; in European Patent Publication EP-A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 47SA1 published Jun. 25, 1997, each of which is incorporated by reference herein in its entirety.

Attenuated viruses generated by the reverse genetics approach can be used in the vaccine and pharmaceutical formulations described herein. Reverse genetics techniques can also be used to engineer additional mutations to other viral genes important for vaccine production—i.e., the epitopes of useful vaccine strain variants can be engineered into the attenuated virus. Alternatively, completely foreign epitopes, including antigens derived from other viral or non-viral pathogens can be engineered into the attenuated strain. For example, antigens of non-related viruses such as HIV (gp160, gp120, gp41) parasite antigens (e.g., malaria), bacterial or fungal antigens or tumor antigens can be engineered into the attenuated strain. Alternatively, epitopes which alter the tropism of the virus in vivo can be engineered into the chimeric attenuated viruses of the invention.

In an alternate embodiment, a combination of reverse genetics techniques and reassortant techniques can be used to engineer attenuated viruses having the desired epitopes in segmented RNA viruses. For example, an attenuated virus (generated by natural selection, mutagenesis or by reverse genetics techniques) and a strain carrying the desired vaccine epitope (generated by natural selection, mutagenesis or by reverse genetics techniques) can be co-infected in hosts that permit reassortment of the segmented genomes. Reassortants that display both the attenuated phenotype and the desired epitope can then be selected.

In another embodiment, the virus to be mutated is a DNA virus (e.g., vaccinia, adenovirus, baculovirus) or a positive strand RNA virus (e.g., polio virus). In such cases, recombinant DNA techniques which are well known in the art may be used (e.g., see U.S. Pat. No. 4,769,330 to Paoletti, U.S. Pat. No. 4,215,051 to Smith each of which is incorporated herein by reference in its entirety).

Any virus may be engineered in accordance with the present invention, including but not limited to the families set forth in Table 1 below.

TABLE 1

| FAMILIES OF HUMAN AND ANIMAL VIRUSES | |
|---|---|
| VIRUS CHARACTERISTICS | VIRUS FAMILY |
| dsDNA | |
| Enveloped | Poxviridae |
|  | Irididoviridae |
|  | Herpesviridae |
| Nonenveloped | Adenoviridae |
|  | Papovaviridae |
|  | Hepadnaviridae |
| ssDNA | |
| Nonenveloped | Parvoviridae |
| dsRNA | |
| Nonenveloped | Reoviridae |
|  | Birnaviridae |
| ssRNA | |
| Enveloped | |
| Positive-Sense Genome | |
| No DNA Step in Replication | Togaviridae |
|  | Flaviviridae |
|  | Coronaviridae |
|  | Hepatitis C Virus |
| DNA Step in Replication | Retroviridae |
| Negative-Sense Genome | |
| Non-Segmented Genome | Paramyxoviridae |
|  | Rhabdoviridae |
|  | Filoviridae |
| Segmented Genome | Orthomyxoviridae |
|  | Bunyaviridae |
|  | Arenaviridae |

TABLE 1-continued

FAMILIES OF HUMAN AND ANIMAL VIRUSES

| VIRUS CHARACTERISTICS | VIRUS FAMILY |
|---|---|
| Nonenveloped | Picornaviridae |
| | Caliciviridae |

Abbreviations used:
ds = double stranded;
ss = single stranded;
enveloped = possessing an outer lipid bilayer derived from the host Cell membrane;
positive-sense genome = for RNA viruses, genomes that are composed of nucleotide sequences that are directly translated on ribosomes, = for DNA viruses, genomes that are composed of nucleotide sequences that are the same as the mRNA;
negative-sense genome = genomes that are composed of nucleotide sequences complementary to the positive-sense strand.

Antisense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

5.4. Vaccine Formulations

The present invention encompasses screening methods to identify viral proteins with interferon antagonist activities, such as influenza virus NS1, ebola virus VP35 and respiratory syncytial virus NS2. Once such interferon antagonist viral proteins have been identified they can be targeted in the virus for mutation or manipulation to create a virus with an impaired interferon antagonist and an attenuated phenotype. While the present invention provides examples of interferon antagonist activities for influenza virus, ebola virus, and respiratory syncytial virus, these are provided by way of example and not limitation. However, the principles of the invention can be analogously applied and extrapolated to other viruses, including other segmented and non-segmented RNA viruses, such viruses may include, but are not limited to paramyxoviruses (Sendai virus, parainfluenza virus, mumps, Newcastle disease virus) morbillivirus (measles virus, canine distemper virus, and rinderpest virus); pneumovirus (respiratory syncytial virus and bovine respiratory virus); rhabdovirus (vesicular stomatis virus and lyssavirus); lentiviruses, including human immunodeficiency virus (HIV), RNA viruses including hepatitis C virus and retroviruses including hepatitis B virus and HIV, virus and HIV, and DNA viruses, including adenovirus, adeno associated virus, hepadna viruses, herpes viruses and poxvirus.

The invention encompasses vaccine formulations comprising attenuated viruses having an impaired ability to antagonize the cellular IFN response, and a suitable excipient. The virus used in the vaccine formulation may be selected from naturally occurring mutants or variants, mutagenized viruses or genetically engineered viruses. Attenuated strains of segmented RNA viruses can also be generated via reassortment techniques, or by using a combination of the reverse genetics approach and reassortment techniques. Naturally occurring variants include viruses isolated from nature as well as spontaneous occurring variants generated during virus propagation, having an impaired ability to antagonize the cellular IFN response. The attenuated virus can itself be used as the active ingredient in the vaccine formulation. Alternatively, the attenuated virus can be used as the vector or "backbone" of recombinantly produced vaccines. To this end, recombinant techniques such as reverse genetics (or, for segmented viruses, combinations of the reverse genetics and reassortment techniques) may be used to engineer mutations or introduce foreign antigens into the attenuated virus used in the vaccine formulation. In this way, vaccines can be designed for immunization against strain variants, or in the alternative, against completely different infectious agents or disease antigens.

Virtually any heterologous gene sequence may be constructed into the viruses of the invention for use in vaccines. Preferably, epitopes that induce a protective immune response to any of a variety of pathogens, or antigens that bind neutralizing antibodies may be expressed by or as part of the viruses. For example, heterologous gene sequences that can be constructed into the viruses of the invention for use in vaccines include but are not limited to epitopes of human immunodeficiency virus (HIV) such as gp120; hepatitis B virus surface antigen (HBsAg); the glycoproteins of herpes virus (e.g. gD, gE); VP1 of poliovirus; antigenic determinants of non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the viruses of the invention. In yet another embodiment, tumor associated antigens may be expressed.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

Vaccine formulations may include genetically engineered negative strand RNA viruses that have mutations in the NS1 or analogous gene including but not limited to the truncated NS1 influenza mutants described in the working examples, infra. They may also be formulated using natural variants, such as the A/turkey/Ore/71 natural variant of influenza A, or B/201, and B/AWBY-234, which are natural variants of influenza B. When formulated as a live virus vaccine, a range of about $10^4$ pfu to about $5\times10^6$ pfu per dose should be used.

Many methods may be used to introduce the vaccine formulations described above, these include but are not limited to intranasal, intratracheal, oral, intradermal, intramuscular, intraperitoneal, intravenous, and subcutaneous routes. It may be preferable to introduce the virus vaccine formulation via the natural route of infection of the pathogen for which the vaccine is designed, or via the natural route of infection of the parental attenuated virus. Where a live influenza virus vaccine preparation is used, it may be preferable to introduce the formulation via the natural route of infection for influenza virus. The ability of influenza virus to induce a vigorous secretory and cellular immune response can be used advantageously. For example, infection of the respiratory tract by influenza viruses may induce a strong secretory immune response, for example in the urogenital system, with concomitant protection against a particular disease causing agent.

A vaccine of the present invention, comprising $10^4$–$5\times10^6$ pfu of mutant viruses with altered IFN antagonist activity, could be administered once. Alternatively, a vaccine of the present invention, comprising $10^4$–$5\times10^6$ pfu of mutant viruses with altered IFN antagonist activity, could be administered twice or three times with an interval of 2 to 6 months between doses. Alternatively, a vaccine of the present invention, comprising $10^4$–$5\times10^6$ pfu of mutant viruses with altered IFN antagonist activity, could be administered as often as needed to an animal, preferably a mammal, and more preferably a human being.

The invention encompasses vaccine formulations comprised of an attenuated virus wherein the attenuation results from a mutation in a gene encoding an interferon antagonist. The invention also encompasses vaccine formulations comprised of an attenuated virus wherein the attenuation results from a mutation in a gene encoding an interferon antagonist in combination with one or more mutations in other viral genes.

The invention also includes vaccine formulations which are chimeric viruses. A chimeric virus could be comprised of any virus where the interferon antagonist gene is derived from either a different virus or a different strain of the same virus. By way of example, but not a limitation a chimeric virus could include an influenza A virus wherein the NS1 gene has been replaced by VP35 from ebola virus. The VP35 gene could contain a mutation which results in an attenuated phenotype of the chimeric virus.

In a preferred embodiment the attenuated virus is respiratory syncytial virus with a mutation in the NS2 gene. An attenuated ebola virus with a mutation in the VP35 would comprise another preferred embodiment. In another preferred embodiment, the attenuated virus is influenza A virus with a mutation in the NS1 gene.

The invention includes a vaccine formulation comprising an attenuated virus for treating or preventing any infectious disease. The infectious disease could be a virus. By way of example, but not as a limitation the vaccine formulation could be used to treat or prevent infection with influenza virus, ebola virus, respiratory syncytial virus, HIV, herpes virus, hepatitis C virus or hepatitis B virus. The infectious disease could consist of a bacterium or a parasite. Additionally the vaccine could be used to treat or prevent cancer or tumor growth.

5.5. Pharmaceutical Compositions

The present invention encompasses pharmaceutical compositions comprising anti-viral agents which are identified by the screening assays described herein to inhibit or modulate viral interferon antagonist activities.

The mutant IFN-inducing viruses of the invention may be engineered using the methods described herein to express proteins or peptides which would target the viruses to a particular site. In a preferred embodiment, the IFN-inducing viruses would be targeted to the site of the infection or the site of entry of the infectious agent. In such an embodiment, the mutant viruses can be engineered to express the antigen combining site of an antibody which recognized the cellular receptor for the infectious pathogen, thus targeting the IFN-inducing virus to the site of the infection. Thus, in accordance with the invention, the IFN-inducing viruses may be engineered to express any target gene product, including peptides, proteins, such as enzymes, hormones, growth factors, antigens or antibodies, which will function to target the virus to a site in need of anti-viral, antibacterial, anti-microbial or anti-cancer activity.

The invention provides methods for the treatment or prevention of viral infections in an animal, preferably a mammal and most preferably a human, said methods comprising the administration of a therapeutically or prophylactically effective amount of an anti-interferon antagonist or nucleic acid molecules encoding said anti-interferon antagonist. Examples of viral infections which can be treated or prevented in accordance with this invention include, but are limited to, viral infections caused by retroviruses (e.g., human T-cell lymphotrophic virus (HTLV) types I and II and human immunodeficiency virus (HIV)), herpes viruses (e.g., herpes simplex virus (HSV) types I and II, Epstein-Barr virus and cytomegalovirus), arenaviruses (e.g., lassa fever virus), paramyxoviruses (e.g., morbillivirus virus, human respiratory syncytial virus, and pneumovirus), adenoviruses, bunyaviruses (e.g., hantavirus), cornaviruses, filoviruses (e.g., Ebola virus), flaviviruses (e.g., hepatitis C virus (HCV), yellow fever virus, and Japanese encephalitis virus), hepadnaviruses (e.g., hepatitis B viruses (HBV)), orthomyoviruses (e.g., Sendai virus and influenza viruses A, B and C), papovaviruses (e.g., papillomavirues), picornaviruses (e.g., rhinoviruses, enteroviruses and hepatitis A viruses), poxviruses, reoviruses (e.g., rotavirues), togaviruses (e.g., rubella virus), and rhabdoviruses (e.g., rabies virus). The treatment and/or prevention of a viral infection includes, but is not limited to, alleviating one or more symptoms associated with said infection, the inhibition, reduction or suppression of viral replication, and/or the enhancement of the immune response.

Compounds identified through assays described, above, in Section 5.1 and 5.2, which inhibit interferon antagonists by decreasing the expression and/or activity of interferon antagonists can be used in accordance with the invention to prevent or treat symptoms associated with viral infections. Further, inhibitors of interferon antagonists can be used to treat viral infections. As discussed above, such compounds can include, but are not limited to nucleic acids, proteins, peptides, phosphopeptides, small organic or inorganic molecules, or antibodies (including, for example, polyclonal, monoclonal, human, humanized, anti-idiotypic, chimeric or single chain antibodies, and Fab, F(ab')$_2$ and Fab expression library fragments, and epitope-binding fragments thereof).

In a specific embodiment, interferon antagonists or fragments representing a functional domain of interferon antagonists are administered to an animal at sufficient dosages such that interferon antagonists activity is decreased in vivo, e.g., by mimicking the function of interferon antagonists in vivo.

The proteins and peptides which may be used in such methods include synthetic (e.g., recombinant or chemically synthesized) proteins and peptides, as well as naturally occurring proteins and peptides. The proteins and peptides may have both naturally occurring and/or non-naturally occurring amino acid residues (e.g., D-amino acid residues) and/or one or more non-peptide bonds (e.g., imino, ester, hydrazide, semicarbazide, and azo bonds). The proteins or peptides may also contain additional chemical groups (e.g., functional groups) present at the amino and/or carboxy termini, such that, for example, the stability, bioavailability, and/or inhibitory activity of the peptide is enhanced. Exemplary functional groups include hydrophobic groups (e.g., carbobenzoxyl, dansyl, and t-butyloxycarbonyl groups) an acetyl group, a 9-fluorenylmethoxy-carbonyl group, and macromolecular carrier groups (e.g., lipid-fatty acid conjugates, polyethylene glycol, or carbohydrates) including peptide groups.

In instances wherein the compound to be administered is a peptide compound, DNA sequences encoding the peptide compound can be directly administered to an animal. Any of the techniques discussed, below, which achieve intracellular administration of compounds, such as, for example, liposome administration, can be utilized for the administration of such DNA molecules. The DNA molecules can be produced, for example, by well known recombinant techniques.

In certain embodiments, a composition of the invention is administered to an animal to ameliorate one or more symptoms associated with a viral infection or a disease or disorder resulting, directly or indirectly, from a viral infection. In a specific embodiment, a composition of the invention is administered to a human to ameliorate one or more symptoms associated with AIDS. In certain other embodiments, a composition of the invention is administered to reduce the titer of a virus in an animal. In certain other embodiments, a composition of the invention is administered to an animal to enhance or promote the immune response.

In a specific embodiment, a composition comprising a therapeutically effective amount of one or more anti-interferon antagonist is administered to an animal in order to ameliorate one or more symptoms associated with a viral infection. In another embodiment, a composition comprising a therapeutically effective amount of one or more anti-interferon antagonist is administered to an animal in order to reduce the titer of a virus in an animal. In another embodiment, a composition comprising a therapeutically effective amount of one or more anti-interferon antagonist and one or more antibodies immunospecific for one or more viral antigens is administered to an animal in order to ameliorate one or more symptoms associated with a viral infection. In yet another embodiment, a composition comprising a therapeutically effective amount of one or more anti-interferon antagonist and one or more antibodies immunospecific for one or more viral antigens is administered to an animal in order to reduce the titer of a virus in an animal.

Anti-interferon antagonist may be administered alone or in combination with other types of anti-viral agents. Examples of anti-viral agents include, but are not limited to: cytokines (e.g., IFN-α, IFN-β, and IFN-γ); inhibitors of reverse transcriptase (e.g., AZT, 3TC, D4T, ddC, ddI, d4T, 3TC, adefovir, efavirenz, delavirdine, nevirapine, abacavir, and other dideoxynucleosides or dideoxyfluoronucleosides); inhibitors of viral mRNA capping, such as ribavirin; inhibitors of proteases such HIV protease inhibitors (e.g., amprenavir, indinavir, nelfinavir, ritonavir, and saquinavir,); amphotericin B; castanospermine as an inhibitor of glycoprotein processing; inhibitors of neuraminidase such as influenza virus neuraminidase inhibitors (e.g., zanamivir and oseltamivir); topoisomerase I inhibitors (e.g., camptothecins and analogs thereof); amantadine; and rimantadine. Such anti-viral agents may be administered to an animal, preferably a mammal and most preferably a human, for the prevention or treatment of a viral infection prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of anti-interferon antagonist to the animal.

In a specific embodiment, one or more anti-interferon antagonist are administered to an animal, preferably a mammal and most preferably a human, for the prevention or treatment of a viral infection prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of plasma to the animal.

In a preferred embodiment, one or more anti-interferon antagonist are administered to an animal, preferably a mammal and most preferably a human, for the prevention or treatment of a viral infection prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of IgG antibodies, IgM antibodies and/or one or more complement components to the animal. In another preferred embodiment, anti-interferon antagonist are administered to an animal, preferably a mammal and most preferably a human, for the prevention or treatment of a viral infection prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of antibodies immunospecific for one or more viral antigens. Example of antibodies immunospecific for viral antigens include, but are not limited to, Synagis®, PRO542, Ostavir, and Protovir.

Methods of introduction include but are not limited to intradermal, intramuscular, intraperitoneal, intravenous, subcutaneous, intranasal, epidural, and oral routes. The pharmaceutical compositions of the present invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in a preferred embodiment it may be desirable to introduce the pharmaceutical compositions of the invention into the lungs by any suitable route. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In yet another embodiment, the pharmaceutical composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N.

Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger & Peppas, 1983, J. Macromol. Sci. Rev. Macromol. Chem. 23:61; see also Levy et al., 1985, Science 228:190; During et al., 1989, Ann. Neurol. 25:351 (1989); Howard et al., 1989, J. Neurosurg. 71:105). In yet another embodiment, a controlled release system can be placed in proximity of the composition's target, i.e., the lung, thus requiring only a fraction of the systemic dose (see, e.g., Goodson, 1984, in Medical Applications of Controlled Release, supra, vol. 2, pp. 115–138). Other controlled release systems are discussed in the review by Langer (1990, Science 249:1527–1533).

The pharmaceutical compositions of the present invention comprise a therapeutically effective amount of an attenuated virus, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. These compositions can be formulated as a suppository. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

The amount of the pharmaceutical composition of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for administration are generally about $10^4$–$5\times10^6$ pfu and can be administered once, or multiple times with intervals as often as needed. Pharmaceutical compositions of the present invention comprising $10^4$–$5\times10^6$ pfu of mutant viruses with altered IFN antagonist activity, can be administered intranasally, intratracheally, intramuscularly or subcutaneously. Effective doses may be extrapolated from dose-response curves derived from in vitro or animal model test systems.

The invention includes a pharmaceutical composition comprising an attenuated virus with an impairment in the interferon antagonist activity. The invention also includes a pharmaceutical composition comprising an attenuated virus with an impairment in the interferon antagonist activity wherein the attenuated virus is a chimeric virus. A chimeric virus could be comprised of any virus where the interferon antagonist gene is derived from either a different virus or a different strain of the same virus. By way of example, but not a limitation a chimeric virus could include an influenza A virus wherein the NS1 gene has been replaced by VP35 from ebola virus. The VP35 gene could contain a mutation which results in an attenuated phenotype of the chimeric virus.

The invention also includes pharmaceutical compositions comprising an anti-viral agent identified by the assays described herein. Said anti-virals would target the viral gene protein that antagonizes interferon function. The anti-viral could be comprised of a protein or peptide, an amino acid, an anti-sense molecule, a ribozyme, any small organic or inorganic molecule.

Methods of introduction of the ant-viral agent include but are not limited to intradermal, intramuscular, intraperitoneal, intravenous, subcutaneous, intranasal, epidural, and oral routes. The pharmaceutical compositions of the present invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in a preferred embodiment it may be desirable to introduce the pharmaceutical compositions of the invention into the lungs by any suitable route. Pulmonary administration can also be employed, e.g., by use of an inhaler or nebulizer, and formulation with an aerosolizing agent.

Any viral infection could be treated with the ant-viral agent, provided that the viral etiological agent contains an interferon antagonist that is sensitive to the anti-viral agent. By way of example, but not by way of limitation, the viral infections that could be treated with an anti-viral agent that targets the interferon antagonist would include influenza virus, respiratory syncytial virus, and ebola virus.

5.6. Demonstration of Therapeutic/Prophylactic Utility of Compositions of the Invention The present invention encompasses pharmaceutical compositions comprising anti-viral agents which are identified by the screening assays described herein to inhibit or modulate viral interferon antagonist activities.

The present invention also encompasses pharmaceutical compositions comprising mutant viruses with altered IFN antagonist activity to be used as anti-viral agents. The pharmaceutical compositions, of the present invention, have utility as an anti-viral prophylactic and may be administered to an individual at risk of getting infected or is expected to be exposed to a virus. For example, in the event that a child comes home from school where he is exposed to several classmates with the flu, a parent would administer the anti-viral pharmaceutical composition of the invention to herself, the child and other family members to prevent viral infection and subsequent illness. People traveling to parts of the world where a certain infectious disease is prevalent (e.g. hepatitis A virus, malaria, etc.) can also be treated.

The compositions of the invention are preferably tested in vitro, and then in vivo for the desired therapeutic or prophylactic activity, prior to use in humans. For example, in vitro assays to demonstrate the therapeutic or prophylactic utility of a composition include, the effect of a composition on a cell line, particularly one characteristic of a specific type of cancer, or a patient tissue sample. The effect of the composition on the cell line and/or tissue sample can be determined utilizing techniques known to those of skill in the art including, but not limited to, rosette formation assays and cell lysis assays. Test compositions can be tested for their ability to augment activated immune cells by contacting activated immune cells with a test composition or a control composition and determining the ability of the test composition to modulate the biological activity of the activated immune cells. The ability of a test composition to modulate the biological activity of activated immune cells can be assessed by detecting the expression of cytokines or antigens, detecting the proliferation of immune cells, detecting the activation of signaling molecules, detecting the effector function of immune cells, or detecting the differentiation of immune cells. Techniques known to those of skill in the art can be used for measuring these activities. For example, cellular proliferation can be assayed by $^3$H-thymidine incorporation assays and trypan blue cell counts. Cytokine and antigen expression can be assayed, for example, by immunoassays including, but are not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electromobility shift assays (EMSAs). The effector function of T-cells can be measured, for example, by a $^{51}$Cr-release assay (see, e.g., Palladino et al., 1987, Cancer Res. 47:5074–5079 and Blachere et al., 1993, J. Immunotherapy 14:352–356).

Test composition can be tested for their ability to reduce tumor formation in patients (i.e., animals) suffering from cancer. Test compositions can also be tested for their ability to reduce viral load or bacterial numbers in vitro and in vivo (e.g., in patients suffering from an infectious disease) utilizing techniques known to one of skill in the art. Test compositions can also be tested for their ability to alleviate of one or more symptoms associated with cancer or an infectious disease (e.g., a viral or microbial infection). Test compositions can also be tested for their ability to decrease the time course of the infectious disease Therapeutic and or prophylactic utility, of the present invention can be demonstrated by way of an in vitro or an in vivo assay. In vitro assays could be performed in any cell line. The cell line could be derived from an animal, insect or plant. Preferably it is derived from an animal and most preferably it is derived from a mammal. Examples of such cell lines include, but are not limited to MDCK, HeLa, Cos, and NIH3T3 cells. In viva assays could be performed in any animal infected with the pathogen of interest. Preferably the animal would be a mammal.

In vitro assays would include any assay that measures the infectious burden of a given pathogen. For example viral load could be measured by any assay known in the art. By way of example, but not as a limitation, a plaque assay or HA assay, or quantitative PCR assay or branched DNA assay could be used.

Infectious burden could be monitored in an in viva assay by any method known in the art including those described above as well as by methods of histology and microscopy. These assays are offered merely as examples and are not intended to be a limitation.

The present invention also provides assays for use in drug discovery in order to identify or verify the efficacy of compounds for treatment or prevention of an infectious disease. Candidate compounds can be assayed for their ability to modulate infectious burden in a subject having an infectious disease. Compounds able to lower the infectious burden in a subject having an infectious disease can be used as lead compounds for further drug discovery, or used therapeutically. Infectious burden can be assayed by immunoassays, gel electrophoresis, plaque assay or any assay that measures viral burden or any other method taught herein or known to those skilled in the art. Such assays can be used to screen candidate drugs, in clinical monitoring or in drug development, where level of infectious burden can serve as a surrogate marker for clinical disease.

In various specific embodiments, in vitro assays can be carried out with cells representative of cell types involved in a disorder, to determine if a compound has a desired effect upon such cell types. For example, HeLa cells or Vero cells can be used to determine if a compound has a desired effect upon such cells.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used. It is also apparent to the skilled artisan that, based upon the present disclosure, transgenic animals can be produced with "knock-out" mutations of the gene or genes encoding any cellular function required by the infectious pathogen or alternatively any immune function that allows the host animal to mount an effective immune response against an infectious pathogen. A "knock-out" mutation of a gene is a mutation that causes the mutated gene to not be expressed, or expressed in an aberrant form or at a low level, such that the activity associated with the gene product is nearly or entirely absent. Preferably, the transgenic animal is a mammal, more preferably, the transgenic animal is a mouse.

In one embodiment, candidate compounds that modulate the level of infectious burden are identified or verified in human subjects suffering from said infectious disease. In accordance with this embodiment, a candidate compound or a control compound is administered to the human subject, and the effect of a test compound on infectious burden is determined by analyzing the level of the infectious pathogen or the mRNA encoding the same in a biological sample (e.g., serum or plasma). A candidate compound that alters the level of the infectious pathogen can be identified by comparing the level of the infectious pathogen or mRNA encoding the same in a subject or group of subjects treated with a control compound to that in a subject or group of subjects treated with a candidate compound. Alternatively, alterations in the infectious burden can be identified by comparing the level of the infectious pathogen or mRNA encoding the same in a subject or group of subjects before and after the administration of a candidate compound. Techniques known to those of skill in the art can be used to obtain the biological sample and analyze the mRNA or protein expression.

In another embodiment, candidate compounds that modulate the level of infectious burden are identified or verified in human subjects having said infectious disease. In accordance with this embodiment, a candidate compound or a control compound is administered to the human subject, and the effect of a candidate compound on the level of the infectious pathogen is determined. A candidate compound that alters the level of infectious burden of the infectious pathogen can be identified by comparing biological samples from subjects treated with a control compound to samples from subjects treated with the candidate compound. Techniques known to those of skill in the art can be used to detect changes in the level of infectious burden, changes or changes in a cellular response to an infectious pathogen. For example, RT-PCR or immunoprecipitation followed by western blot analysis can be used to detect changes in the level of infectious burden.

In another embodiment, candidate compounds that reduce the severity of one or more symptoms associated with an infectious pathogen are identified in human subjects having said infectious pathogen. In accordance with this embodiment, a candidate compound or a control compound is administered to a human subject, suffering from an infectious pathogen and the effect of a candidate compound on one or more symptoms of the infectious pathogen is determined. A candidate compound that reduces one or more symptoms can be identified by comparing the subjects treated with a control compound to the subjects treated with the test compound. Techniques known to physicians familiar with infectious diseases can be used to determine whether a candidate compound reduces one or more symptoms associated with the infectious disease.

5.7. Demonstration of the Ability of Viral Interferon Antagonists to Enhance Translation The present invention relates to the ability of viral interferon antagonists to enhance translation of mRNAs. The interferon antagonists identified by the screening assays of the present invention have utility in in vitro and in vivo protocols to enhance levels of translation. Such in vitro and in vivo protocols may include: (1) enhancing levels of translation in assay systems where enhanced translation levels are required, such as reporter assay systems where enhanced sensitivity is required; (2) enhancing levels of translation in cell based assays to increase detection of a target protein; (3) ex vivo based gene therapy protocols, to increase detection of a marker or increase expression of a target gene; and (4) in vivo based gene therapy protocols to increase detection of a marker or increase expression of a target gene.

The in vitro and in vivo protocols involving the use of interferon antagonists to enhance levels of translation encompass research based assays, highthroughput screening assays, drug screening assays, in vitro, ex vivo, and in vivo diagnostic, prophylactic and therapeutics assays and protocols.

Any interferon antagonist identified by the assays of the present invention may be used in this embodiment. In a preferred embodiment, the interferon antagonist used to enhance translation is NS2 of respiratory syncytial virus or VP35 of ebola virus. In a most preferred embodiment, the interferon antagonist is the NS1 protein of influenza A virus.

5.8. Kits

The present invention provides for kits that can be used in the above methods. In one embodiment the kit would be comprised of a virus, contained in an appropriate package, with impaired interferon antagonist activity. As an example, but not as a limitation the delNS1 influenza A virus mutant could be used. The kit would also contain a positive control, in an appropriate package, consisting of a viral interferon antagonist. By way of example, but not as a limitation the viral interferon antagonist could include NS2 of respiratory syncytial virus, VP35 of ebola virus or NS1 of influenza A virus. The kit would also contain a negative control. The kit would also contain an appropriate plasmid or vector to express the positive and or negative control. Also included in the kit would be a reporter construct, in an appropriate package, that is linked to an interferon responsive element. The reporter construct could be the luciferase gene for example, but not as a limitation. The kit would also contain instructions for use.

6. EXAMPLE

Transfection of Viral Interferon Antagonists Complements Growth of Influenza DeInsl Virus: a Method to Identify Novel Interferon Antagonists The following example demonstrates the use of a virus with impaired interferon antagonist activity, such as influenza delNS1 virus, to screen for viral proteins with interferon antagonist activities. The example describes the use of such an impaired virus to assay for the ability of viral protein to complement growth of the impaired virus, that is, the ability of the viral protein to provide interferon antagonist activity.

Thus, the following complementation assay was devised as an example of an assay that could be used to test the ability of exogenous viral proteins to compensate for the delNS1 influenza A virus mutant's inability to antagonize cellular interferon type I function.

6.1. Expression in MDCK Cells of the PR8 NS1 Protein Complements Growth of delNS1 Virus The delNS1 virus grows poorly on MDCK cells compared with the wild-type PR8 influenza virus, a virus syngeneic with delNS1 virus except that it produces the NS1 protein. It was therefore determined whether high efficiency transfection of MDCK cells with an NS1-expression plasmid would complement growth of delNS1 virus. MDCK cells were transfected using Lipofectamine™2000 (GibcoBRL®) to introduce either an empty vector (pCAGGS) or an NS1 expression plasmid (pCAGGS-PR8 NS1 SAM) (Talon et al. 2000 J.Virol. 74 (17):7989–96). ("SAM" (spliceacceptor mutant) indicates that the splice acceptor within the NS1 ORF was mutated to prevent expression of an alternatively spliced message from the NS1 gene.) Sixteen hours post-transfection, the cells were infected with either wild-type PR8 or delNS1 virus at a multiplicity of infection (moi) of 0.001. As a negative control, NS1-transfected cells were left uninfected. Forty-eight hours post-transfection an HA assay was performed to determine viral titers (Table 2).

TABLE 2

Transfection of an NS1-expression plasmid complements growth on MDCK cells of delNS1 virus.

| Plasmid | Virus | HA titer |
|---|---|---|
| Empty vector | delNS1 | 0 |
| pCAGGS-NS1 SAM | delNS1 | 128 |
| Empty vector | PR8 | 32 |
| pCAGGS-NS1 SAM | PR8 | 128 |
| pCAGGS-NS1 SAM | none | 0 |

While delNS1 virus-infected, empty vector-transfected cells did not produce a detectable HA titer, the delNS1-infected, NS1-transfected cells yielded an HA titer equal to that achieved by infection with wild-type PR8. No HA titer was obtained when virus infection was omitted. Thus, the restricted growth of delNS1 virus on interferon-producing MDCK cells can be greatly enhanced by transfection of an NS1 expression plasmid.

6.2. Expression in MDCK Cells of the Influenza B Virus and Influenza C Virus NS1 Proteins also Complements Growth of delNS1 Virus Based on the results in part 6.1, complementation of delNS1 growth should also be possible following expression of other interferon antagonists. The influenza A, B and C NS1 proteins show little sequence identity to one another. However, the influenza B virus NS1 protein is able to bind RNA and to inhibit activation of PKR (Wang et al. 1999 Virology 223(1):41–50). In addition, influenza B viruses encoding truncated NS1 proteins have diminished ability to grow in interferon producing embryonated chicken eggs. No data regarding the ability of the influenza C virus NS1 protein to bind RNA or inhibit PKR have been reported. Furthermore, no data regarding the ability of influenza C virus NS1 protein to antagonize interferon responses have been reported.

Thus, the NS1 proteins encoded by the influenza B and C viruses were tested for delNS1 complementing activity. MDCK cells were transfected as described above with an empty vector (pCAGGS), with the PR8 NS1 expression plasmid (pCAGGS-PR8 NS1 SAM), a B/Yamagata/73 virus NS1 expression plasmid (pCAGGS B NS1 SAM) or a C/Jhb/66 virus NS1 expression plasmid (pCAGGS-C NS1 SAM). Sixteen hours post-transfection, the cells were infected with delNS1 virus at an moi of 0.001. Tissue culture supernatants were harvested forty eight hours post-infection. Plaque assays were then performed to determine whether the A, B or C virus NS1 proteins complemented growth of delNS1 virus (Table 3). The results indicate that both the influenza B virus and the influenza C virus NS1 proteins, like the influenza A virus NS1 protein, can inhibit interferon-mediated antiviral responses.

TABLE 3

Complementation of delNS1 virus growth by influenza B virus NS1, influenza C virus NS1 and vaccinia virus E3L proteins.

| Plasmid | Virus | Titer (pfu/ml) |
|---|---|---|
| Empty vector | delNS1 | $2 \times 10^2$ |
| pCAGGS-PR8 NS1 SAM | delNS1 | $2.5 \times 10^6$ |
| pCAGGS-B/Yam NS1 SAM | delNS1 | $3.7 \times 10^5$ |
| pCAGGS-C/Jhb NS1 SAM | delNS1 | $2.8 \times 10^5$ |
| pCAGGS-E3L | delNS1 | $1 \times 10^5$ |

*Titer obtained by plaque assay 48 hours post-infection

6.3 Expression in MDCK Cells of the Vaccinia Virus E3L Protein also Complements Growth of delNS1 Virus The vaccinia virus E3L protein is a dsRNA binding protein which can also interact directly with PKR (Chang et al. 1992 Proc. Natl. Acad. Sci. USA 89 (11):4825–9; Davies et al. 1993 J. Virol. 67 (3):1688–92; Romano et al. 1998 Mol. Cell. Biol. 18 (12):7304–16; Sharp et al. 1998 Virology 250 (2):302–15). E3L is able to inhibit PKR activity (Chang et al. 1992 Proc. Natl. Acad. Sci. USA 89 (11):4825–9), to inhibit OAS (Rivas et al. 1998 Virology 243 (2):406–14) and to protect vaccinia virus from the effects of interferon (Beattie et al. 1995 J. Virol. 69 (1)499–505; Shors et al. 1998 J. Interferon Cytokine Res. 18 (9): 721–9). If the influenza A, B and C virus NS1 proteins enhance growth of delNS1 virus on MDCK cells by inhibiting interferon responses, then the vaccinia virus E3L protein would also be predicted to complement delNS1 virus growth. Transfected E3L expression plasmid was indeed able to enhance growth of delNS1 virus on MDCK cells (Table 3).

It was determined that expression of another known inhibitor of the type I IFN-induced antiviral response, HSV-1 ICP34.5, complements growth of influenza delNS1 virus. Expression of the HSV-1-encoded PKR antagonist ICP34.5 (Garcia-Sastre et al. 1998 Virology 252 (2):324–30) clearly complemented growth of the influenza delNS1 virus (FIG. 5). This result indicated that complementation of influenza delNS1 virus growth reflects an anti-IFN function. This result also indicates that interferon antagonists encoded by viruses other than orthomyxoviruses can be identified using the screening assays of the present invention.

7. EXAMPLE

Expression in MDCK Cells of the Ebola Virus VP35 Protein Complements Growth of Delns1 Virus Ebola viruses are enveloped, negative-strand RNA viruses belonging to the family Filoviridae. These viruses possess genomes of approximately 19 kb and are known to encode eight proteins, the nucleoprotein (NP), VP35, VP40, glycoprotein (GP), soluble GP, VP30, VP24, and L (polymerase) proteins (Klenk et al. 1994 Encyclopedia of Virology Academic, New York vol 2: 827–31). Ebola virus infections frequently result in severe hemorrhagic fever, and epidemics of the Ebola virus, Zaire subtype have resulted in mortality rates of greater than 80% (Klenk et al. 1994 Encyclopedia of Virology, Academic, New York, vol 2: 827–31; Peters et al. 1999 Curr Top. Microb Immunol. 235:85–95). The pathologic features and the immune responses characteristic of fatal and nonfatal human Ebola virus infections have begun to be characterized (Villinger et al. 1999 J. Infect. Dis. 179 Suppl. 1:S188–191; Yang et al. 1998 Science 279:1034–37). In order to determine if an ebola viral protein exhibits interferon antagonist activity, the influenza delNS1 virus complementation assay was used to screen for an ebola virus encoded interferon antagonist.

7.1. Materials and Methods

Influenza delNS1 virus complementation assay. High-efficiency transient transfection of MDCK cells was performed by using Lipofectamine 2000™ (LF2000) (GIBCO/BRL). Four micrograms of the indicated expression plasmid was adjusted to fifty microliters by Optimum I medium (GIBCO/BRL). Per transfection ten microliters of LF2000 was adjusted to 0.25 ml with Optimum I medium and incubated in a five ml polystyrene snap-cap tube at room temperature for five minutes. Each fifty microliter DNA sample was added to the 0.25 ml LF2000/Optimum I mix agitated gently, and incubated twenty minutes at room temperature. A confluent 80 cm² lask of MDCK cells was detached with trypsin. The cells were brought to 12 ml wit hDMEM/10% fetal bovine serum (no antibiotics), pelleted at one thousand rpm for five minutes in a table top centrifuge and after aspiration of the supernatant resuspended in DMEM/10% Fetal bovine serum (no antibiotics) to a concentration of $4 \times 10^6$ cells/ml. A portion (0.25 ml) of the cell suspension was aliquoted in 35 mm tissue culture dishes. After twenty minutes incubation period one ml Of DMEM/ 10%FBS (no antibiotics) was added to each DNA/LF2000 mix and the DNA/LF2000 medium mixture was added to dishes containing the MDCK cells. After mixing the cells were maitained at 37° C. overnight. Sixteen to twenty hours posttransfection the cells were infected with $10^3$ plaque forming units (PFU) of influenza delNS1 virus (multiplicity of infection=0.001) in a volume of 0.1 ml. After removal of the inoculum, the cells were maintained in 1.5 ml DMEM/ 0.3% bovine albumin/3 micrograms/ml trypsin (trypsin 1:250;Difco)

7.2. Results

To identify potential Ebola virus-encoded interferon antagonists, plasmids encoding Ebola virus proteins were screened for their ability to complement growth of the delNS1 virus on MDCK cells (Table 4). Expression of the Ebola virus VP35 protein in MDCK cells was found to stimulate growth of the mutant influenza virus more than one thousand-fold. Therefore, the Ebola virus VP35 is likely to function as an interferon antagonist in Ebola virus infected cells.

TABLE 3

Complementation of delNS1 virus growth by Ebola virus proteins.

| Expressed protein | pfu/ml |
|---|---|
| Empty vector | 10 |
| NS1 | $1.2 \times 10^6$ |
| NP | 10 |
| VP35 | $1.9 \times 10^4$ |
| VP40 | <10 |
| GP | <10 |
| sGP | 20 |
| VP30 | <10 |
| VP24 | <10 |

The Ebola Virus VP35 Protein Complements Growth of Influenza delNS1 Protein. The influenza delNS1 virus complementation assay then was used to screen for an Ebola virus-encoded IFN antagonist. An empty vector, the NS1-expression plasmid, or plasmids encoding individual Ebola virus proteins were transfected into MDCK cells. Twenty-four hours posttransfection, the cells were infected with influenza delNS1 virus. Forty-eight hours postinfection, the supernatants were harvested and viral titers were determined by plaque assay (Table 4). The only Ebola virus protein that enhanced influenza delNS1 virus growth was the VP35 protein (Table 4). Time-course analysis clearly demonstrated the enhancement of influenza delNS1 virus growth by VP35 (FIG. 6).

Expression of the Ebola Virus VP35 Protein Blocks Induction of an ISRE Promoter. To determine whether VP35 inhibits the dsRNA- and virus-mediated activation of IFN-sensitive gene expression, cells were transfected with an ISRE-driven CAT-reporter plasmid and a constitutively expressed, simian virus 40 promoter-driven luciferase reporter plasmid. Additionally, the cells were transfected with empty vector, NS1 expression plasmid, VP35 expression plasmid, or, as an additional control, an Ebola virus NP expression plasmid. One day later, the cells were mock-treated, transfected with dsRNA, or infected with either influenza delNS1 virus or with Sendai virus, strain Cantell (an attenuated strain known to induce large amounts of IFN). After an additional twenty four hours, cell lysates were prepared and assayed for CAT activity and luciferase activity (FIG. 7A). Transfection of cells with dsRNA or infection with either influenza delNS1 virus or Sendai virus gave a strong induction of the IFN-sensitive promoter. When either NS1 or VP35 was present, expression from the IFN-responsive promoter was almost completely blocked. Levels of ISRE induction, normalized to levels of luciferase activity, are shown in FIG. 7A. Expression of the control luciferase reporter plasmid was not inhibited by expression of either NS1 or VP35. Expression of the Ebola virus NP, which did not complement growth of influenza delNS1 virus, did not inhibit activation of the ISRE promoter. Expression of the NS1, VP35, and NP proteins was confirmed by Western blotting (FIG. 7B). These results show that both NS1 and VP35 can block type I IFN production and/or signaling in response to either dsRNA treatment or to viral infection.

Expression of the Ebola Virus VP35 Protein Blocks Activation of the INF-β Promoter. In wild-type influenza A virus-infected cells, the NS1 protein blocks induction of type I IFN. This block is due, in large part, to the ability of NS1 to prevent activation of IRF-3 and NF-B, two transcription factors that play a critical role in stimulating the synthesis of IFN-β. Synthesis of IFN-β, in turn, plays an important role in the initiation of the type I IFN cascade (Marie et al. 1998 EMBO J. 17:6660–69). The Ebola virus VP35, therefore, was tested for its ability to block activation of the IFN-β promoter.

Empty vector, NS1 expression plasmid, or VP35 expression plasmid was cotransfected with a mouse IFN-β promoter-driven CAT reporter and a simian virus 40 promoter-driven luciferase reporter. When cells subsequently were transfected with dsRNA, a strong induction of the IFN-β promoter was observed in empty vector-transfected cells, but this induction was blocked when either NS1 or VP35 was expressed (FIG. 8A). It also was determined whether VP35 could block activation of the endogenous human IFN-β promoter. Cells were transfected with empty vector or VP35 expression plasmid and, twenty four hours later, mock-infected or infected with influenza delNS1 virus or with Sendai virus. Ten or twenty hours postinfection, total cellular RNA was isolated, and a Northern blot was performed to detect IFN-mRNA (FIG. 8B). Expression of VP35 clearly blocked induction of the endogenous IFN-β promoter. Before infection with either virus, IFN-β mRNA was undetectable. After infection, when the IFN-β mRNA levels were normalized to β-actin mRNA levels, it was found that, in influenza delNS1 virus-infected cells, the presence of VP35 reduced IFN-β induction 8-fold at ten hours postinfection and 8.4-fold at twenty hours posttransfection. In Sendai virus-infected cells, the presence of VP35 reduced IFN-induction 6.1-fold at ten hours post-transfection and 5.9-fold at twenty hours posttransfection.

The Ebola Virus VP35 Blocks INF Induction When Coexpressed with the Ebola Virus NP. The VP35 protein is an essential component of the Ebola virus RNA synthesis complex and likely associates with the viral NP (Muhlberger et al. 1999 J. Virol. 73:2333–42; Becker et al. 1998 Virology 249:406–17). Therefore, it was determined whether Ebola virus VP35 retained its IFN-antagonizing properties when it was coexpressed with the Ebola virus NP. An ISRE-reporter assay was performed in which cells received either empty vector, VP35 alone, NP alone, or a combination of VP35 and NP. Twenty-four hours posttransfection, the cells were transfected with dsRNA or infected with Sendai virus. As seen previously, transfection with empty plasmid or with NP expression plasmid did not block activation of the ISRE promoter, but expression of VP35 did block its activation (FIG. 9). Further, coexpression of VP35 and NP was able to block ISRE activation to the same extent as expression of VP35 alone (FIG. 9). These data indicate that VP35, even when coexpressed with the Ebola virus NP, can act as an IFN antagonist.

The Ebola virus VP35 protein inhibits type I IFN induction when coexpressed with Ebola virus NP (FIG.9). Fold induction of the IFN-inducible ISRE-driven reporter in the presence of empty vector, VP35, NP, or VP35 plus NP. 293 cells were transfected with a total of 4 μg of expression plasmid, including 2 μg of a plasmid encoding an individual protein and 2 μg of a second plasmid (either empty vector or a second expression plasmid) plus 0.3 μg each of the reporter plasmids pHISG-54-CAT and pGL2-Control. Twenty-four hours posttransfection, the cells were mock-treated or treated with the indicated IFN inducer. Twenty-four hours postinduction, CAT and luciferase assays were performed. The CAT activities were normalized to the corresponding luciferase activities to determine fold induction.

The production of an IFN antagonist contributes to the virulence of Ebola viruses. In humans, it appears that an appropriate cytokine response is related to the development of asymptomatic or nonfatal Ebola virus infection. Thus, a viral factor that influences type I IFN production influences viral pathology.

8. EXAMPLE

Complementation of Growth of Interferon-sensitive Viruses by Expression of an Interferon Antagonist, the Influenza A Virus NS1 Protein In the example below an influenza A NS1 (PR8) was shown to enhance the growth of a virus with impaired interferon antagonist activity.

8.1. Influenza C Virus Growth is Restricted in Embryonated Chicken Eggs that Produce an Interferon Response Influenza C virus was tested for its ability to grow in 7-day old versus 11-day old embryonated chicken eggs. Young embryos, such as 7-day old embryos, produce little interferon in response to viral infection while older embryos, such as 11-day old embryos, produce higher levels of interferon in response to viral infection (Sekellick et al. 1990 In vitro Cell Biol. 26:997–1003). Replication of influenza C/Jhb/66 virus was found to be significantly more efficient in the younger eggs (Table 5). These data strongly suggest that growth of influenza C virus is restricted by interferon.

TABLE 5

Growth of influenza C/Jhb/66 virus in 7 - and 11-day old embryonated chicken eggs.*

| Age of embryo (days) | HA titer |
| --- | --- |
| 7 | 512 |
| 11 | 4 |

*Eggs were inoculated with 500 pfu of virus and incubated for 3 days at 33° C.

8.2. Expression in MDCK Cells of the PR8 NS1 Protein Enhances Growth of Influenza C Virus Given the sensitivity of influenza C virus to interferon, the ability of a potent interferon antagonist (the influenza A virus NS1 protein) to enhance influenza C virus growth on MDCK cells was tested. The experiment was performed similarly to that described for delNS1 virus except that transfected cells were infected with influenza C/Jhb/66 virus (moi.=0.001) instead of delNS1 virus. The results are shown in Table 6.

TABLE 6

Expression of the influenza A virus NS1 protein complements growth of influenza C virus on MDCK cells.

| Plasmid | HA titer |
| --- | --- |
| Empty plasmid | 2 |
| pCAGGS-PR8 NS1 | 32 |

Thus expression of a potent viral interferon antagonist can enhance growth of viruses which are sensitive to the effects of interferon. The expression of the viral interferon antagonist may be used for the isolation, growth and analysis of interferon-sensitive viruses.

9. EXAMPLE

Complementation of Growth of an Interferon-sensitive Virus by an Interferon Antagonist Derived from a Paramyxovirus In the example below, respiratory syncytial virus (RSV) NS2 was shown to be an interferon antagonist using the screening assays described herein. The expression of RSV NS2 was shown to support the growth of an attenuated non-RSV virus with impaired interferon antagonist activity.

9.1 Expression in MDCK Cells of the Respiratory Syncytial Virus (RSV) NS2 Protein Complements Growth of delNS1 Virus Human RSV is the leading cause of severe viral respiratory infections in children. Although it has been reported that the NS1 and NS2 proteins of bovine RSV have interferon antagonistic properties the human RSV gene products responsible for antagonizing interferon are unknown. To identify potential human RSV-encoded interferon antagonists, plasmids encoding human RSV proteins were screened for their ability to complement growth of the delNS1 virus on MDCK cells(Table 7). Expression of the human RSV NS2 protein in MDCK cells was found to stimulate growth of the mutant influenza virus. Therefore, the human RSV NS2 protein functions as an interferon antagonist.

TABLE 7

RSV N2 complements growth of del Ns1 Virus

| Plasmid | Virus | HA titer |
| --- | --- | --- |
| Empty vector | delNS1 | 0 |
| pCDNA3-PR8NS1 SAM | delNS1 | 128 |
| pcDNA3-hRSV NS2 | delNS1 | 16 |

Titer obtained by hemagglutination assay 48 hours post infection

10. EXAMPLE

Co-Transfection of the Influenza A Virus NS1 Protein Enhances Expression from Co-Transfected Expression Plasmids The following example demonstrates the ability of an interferon antagonist to enhance translation of mRNAs.

The influenza A virus NS1 protein has been reported to enhance translation of mRNAs (de la Luna et al. 1995 J.Virol. 67 (4):2427–33; Enami et al. 1994 J. Virol. 68 (3):1432–37). This ability is likely related to its ability to inhibit activation of the interferon-induced dsRNA-activated protein kinase, PKR (Hatada et al. 1999 J. Virol. 73 (3):2425–33). However, it is not clear whether NS1 inhibits PKR by sequestering dsRNA (Lu et al. 1999 Virology 214 (1):222–28), by interacting directly with PKR (Tan et al. 1998 J. Interferon Cytokine Res. 18 (9):757–66) or by a combination of the two mechanisms. The ability to enhance translation is a property characteristic of several viral-encoded PKR inhibitors, including adenovirus VA $RNA_1$ (Svensson et al. 1985 EMBO J.4 (4):957–64) the vaccinia virus E3L protein (Davies et al. 1993 J. Virol. 67 (3):1688–92), and perhaps the hepatitis C virus NS5A protein (Gale et al. 1997 Virology 230 (2):217–27). These proteins also appear to confer interferon-resistance to the viruses (Beattie et al., 1995 J. Virol 69 (1):499–505; Kitajewski et al. 1986 Cell 45 (2):195–200).

Therefore, the ability of the PR8 NS1 expression plasmid to enhance expression from a co-transfected reporter plasmid was tested. 293T cells were transfected with a total of 6 μg DNA. The 6 μg consisted of 4 μg pGL2-Control (Promega Corp.) (an SV40-promoter-driven, constitutively expressed luciferase reporter plasmid), 1 μg pEGFP-c1 (Clonetech Laboratories) (a CMV-promoter-driven green fluorescence protein (GFP) expression plasmid) and a combination of pCAGGS and pCAGGS-PR8 NS1 SAM totaling 1 μg. Transfections were performed containing 0, 1, 0.2 and 0.04 μg NS1 expression plasmid. Forty eight hours post-transfection, the cells were observed for GFP expression to confirm that dishes were transfected at comparable levels, and luciferase assays were performed. NS1-expression plasmid gave a 19.8-fold maximal stimulation of luciferase expression, and the enhancement was dose-dependent (FIG. 5).

Thus, interferon antagonists identified using the screening assays described herein have utility in enhancing translation of mRNAs in in vitro and in vivo applications.

The present invention is not to be limited in scope by the exemplified embodiments, which are intended as illustrations of single aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed:

1. A screening method for identifying an RNA viral polypeptide with an interferon-antagonizing function comprising:
   (a) contacting a cell which expresses a viral protein with interferon antagonizing function, with an RNA virus containing a mutation that results in a decrease in activity of a viral polypeptide;
   (b) determining if growth of said RNA virus in the cell is enhanced by the presence of the viral protein with interferon antagonizing function; and
   (c) if growth of said RNA virus is enhanced, identifying the viral polypeptide as having an interferon antagonizing function.

2. The screening method of claim 1, wherein the RNA virus is a paramyxovirus.

3. The screening method of claim 2, wherein the paramyxovirus is selected from a group consisting of Sendai virus, parainfluenza virus, mumps, and Newcastle disease virus.

4. The screening method of claim 1, wherein the RNA virus is a morbillivirus.

5. The screening method of claim 4, wherein the morbillivirus is selected from a group consisting of measles virus, canine distemper virus, and rinderpest virus.

6. The screening method of claim 1, wherein the RNA virus is a pneumovirus.

7. The screening method of claim 6, wherein the pneumovirus is selected from a group consisting of respiratory syncytial virus and bovine respiratory virus.

8. The screening method of claim 1, wherein the RNA virus is a rhabdovirus.

9. The screening method of claim 8, wherein the rhabdovirus is selected from a group consisting of vesicular stomatitis virus and lyssavirus.

10. The screening method of claim 1 wherein the viral protein is influenza virus NS1.

11. The screening method of claim 1 wherein the viral protein is respiratory syncytial virus NS2.

12. The screening method of claim 1 wherein the viral protein is Ebola virus VP 35.

13. A screening method for identifying an RNA viral protein with an interferon-antagonizing function comprising:
   (a) contacting a cell which expresses an RNA viral protein with an RNA virus containing a mutation that results in a decrease in activity of a viral interferon antagonist;
   (b) determining if growth of the mutant RNA virus in the cell is enhanced by the presence of the RNA viral protein; and
   (c) if growth of the mutant RNA virus is enhanced, identifying the RNA viral protein as having an interferon antagonizing function.

14. The screening method of claim 13, wherein the mutant RNA virus is an influenza virus with NS1 deleted.

15. The screening method of claim 13, wherein the cell has been transfected with a plasmid encoding the viral protein.

16. A screening method for identifying a viral protein with an interferon-antagonizing function comprising:
   (a) contacting a cell which expresses influenza virus NS1 protein, with a virus containing a mutation that results in a decrease in activity of a viral polypeptide;
   (b) determining if growth of the mutant virus in the cell is enhanced by the presence of NS1 protein; and
   (c) identifying the viral polypeptide as having an interferon antagonizing function.

17. A screening method for identifying a viral polypeptide with an interferon-antagonizing function comprising:
   (a) expressing the viral polypeptide in a cell and infecting the cell with a deINS1 mutant influenza virus;
   (b) determining if growth of the mutant influenza virus is enhanced by the expression of the viral protein; and
   (c) if growth is enhanced by the expression of the viral polypeptide, identifying the viral polypeptide as having an interferon antagonizing function.

* * * * *